(12) United States Patent
Izmailov et al.

(10) Patent No.: US 11,305,274 B2
(45) Date of Patent: Apr. 19, 2022

(54) DISPOSABLE BIOASSAY CARTRIDGE AND METHOD OF PERFORMING MULTIPLE ASSAY STEPS AND FLUID TRANSFER WITHIN THE CARTRIDGE

(71) Applicant: AXELA INC., Etobicoke (CA)

(72) Inventors: Alexandre Izmailov, Etobicoke (CA); David Englert, West Hartford, CT (US); Paul Smith, Acton (CA)

(73) Assignee: ANGLE EUROPE LIMITED, Guildford (GB)

( * ) Notice: Subject to any disclaimer, the term of this patent is extended or adjusted under 35 U.S.C. 154(b) by 0 days.

(21) Appl. No.: 15/902,030

(22) Filed: Feb. 22, 2018

(65) Prior Publication Data
US 2019/0054460 A1 Feb. 21, 2019

Related U.S. Application Data

(62) Division of application No. 15/564,791, filed as application No. PCT/CA2016/050414 on Apr. 11, 2016, now Pat. No. 10,946,375.
(Continued)

(51) Int. Cl.
*B01L 3/00* (2006.01)
*C12M 1/00* (2006.01)
(Continued)

(52) U.S. Cl.
CPC .......... *B01L 3/502* (2013.01); *B01L 3/50273* (2013.01); *B01L 7/52* (2013.01); *C12M 23/28* (2013.01); *C12M 25/14* (2013.01); *C12M 41/40* (2013.01); *B01L 2200/025* (2013.01); *B01L 2200/026* (2013.01); *B01L 2200/0621* (2013.01);
(Continued)

(58) Field of Classification Search
None
See application file for complete search history.

(56) References Cited

U.S. PATENT DOCUMENTS 5,262,021 A 11/1993 Lehmann
5,423,581 A * 6/1995 Salyers ................. F16L 33/223
285/137.11
(Continued)

FOREIGN PATENT DOCUMENTS

JP 2003166910 6/2003
JP 2004261779 A 9/2004
(Continued)

OTHER PUBLICATIONS

Lehmann et al., "The Physics of Macropore Formation in Low-Doped p-Type Silicon", V. Lehmanna, and S. Rönnebeck; Journal of The Electrochemical Society, 146 (8) 2968-2975 (1999).
(Continued)

*Primary Examiner* — Matthew D Krcha
(74) *Attorney, Agent, or Firm* — Hill & Schumacher

(57) ABSTRACT

The present disclosure provides a cartridge and method to move fluids within the cartridge that simplifies the design and removes the need for any internal valves or metering devices. The design is amenable to injection molded manufacturing lowering cost for large volume manufacturing. The design can be adapted to carry out both sample preparation and detection of biological substances including nucleic acids and proteins.

20 Claims, 25 Drawing Sheets

Related U.S. Application Data

(60) Provisional application No. 62/165,347, filed on May 22, 2015, provisional application No. 62/145,330, filed on Apr. 9, 2015.

(51) Int. Cl.
  *C12M 1/12* (2006.01)
  *C12M 1/34* (2006.01)
  *B01L 7/00* (2006.01)

(52) U.S. Cl.
  CPC ............... *B01L 2200/0684* (2013.01); *B01L 2200/0689* (2013.01); *B01L 2200/147* (2013.01); *B01L 2200/16* (2013.01); *B01L 2300/0681* (2013.01); *B01L 2300/0874* (2013.01); *B01L 2400/0406* (2013.01); *B01L 2400/0487* (2013.01); *B01L 2400/0683* (2013.01); *B01L 2400/084* (2013.01)

(56) References Cited

U.S. PATENT DOCUMENTS

| | | | |
|---|---|---|---|
| 5,882,496 A | 3/1999 | Northrup et al. | |
| 6,383,748 B1 | 5/2002 | Carpay et al. | |
| 6,602,397 B1* | 8/2003 | Hofmann | B01D 67/0058 |
| | | | 205/655 |
| 6,770,322 B1* | 8/2004 | Moles | C12Q 1/001 |
| | | | 427/230 |
| 6,849,408 B2 | 2/2005 | Carpay et al. | |
| 2003/0062657 A1* | 4/2003 | Parameswaran | B01D 69/00 |
| | | | 264/553 |
| 2004/0142463 A1* | 7/2004 | Walker | B01D 61/18 |
| | | | 435/325 |
| 2005/0241477 A1* | 11/2005 | Mundschau | B01D 53/228 |
| | | | 95/56 |
| 2012/0037591 A1* | 2/2012 | Tringe | B01D 67/0062 |
| | | | 216/2 |
| 2013/0239813 A1* | 9/2013 | Rakow | B01D 53/0415 |
| | | | 96/108 |

FOREIGN PATENT DOCUMENTS

| | | | |
|---|---|---|---|
| JP | 2006149215 | 6/2006 | |
| JP | 2006162592 | 6/2006 | |
| JP | 2007097444 | 4/2007 | |
| JP | 2007520692 | 7/2007 | |
| JP | 2009500602 | 1/2009 | |
| JP | 2014417909 | 7/2014 | |
| JP | 2014517909 | 7/2014 | |
| WO | 0230561 | 4/2002 | |
| WO | WO-0230561 A2 * | 4/2002 | ............ B01L 3/5025 |
| WO | 03089931 | 10/2003 | |
| WO | 2014182847 | 11/2014 | |
| WO | 2015015178 | 2/2015 | |

OTHER PUBLICATIONS

Granitzer et al., "Porous Silicon—A Versatile Host Material", Petra Granitzer and Klemens Rumpf Materials 2010, 3, 943-998; doi:10.3390/ma3020943.

Foll et al, "Formation and application of porous silicon", H. Foll, M. Christophersen, J. Carstensen, G. Hasse Materials Science and Engineering R 280 (2002) 1-49.

* cited by examiner

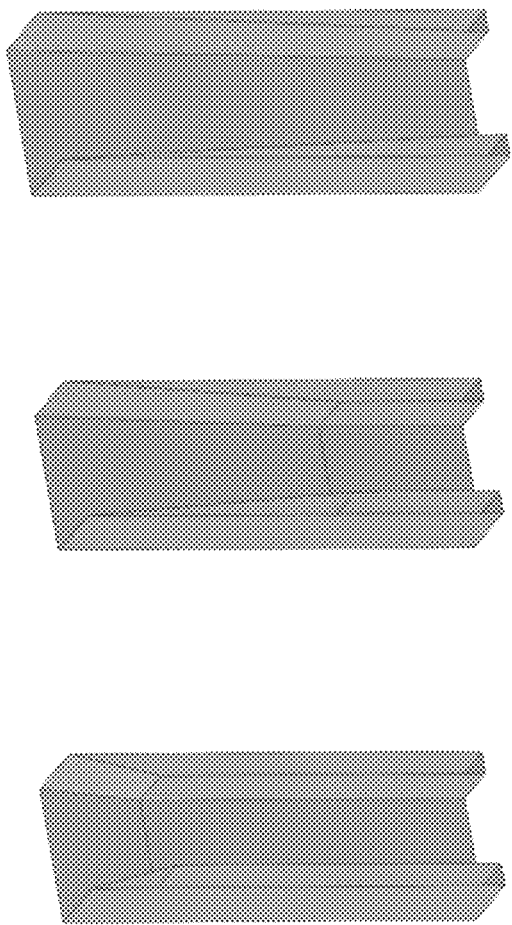

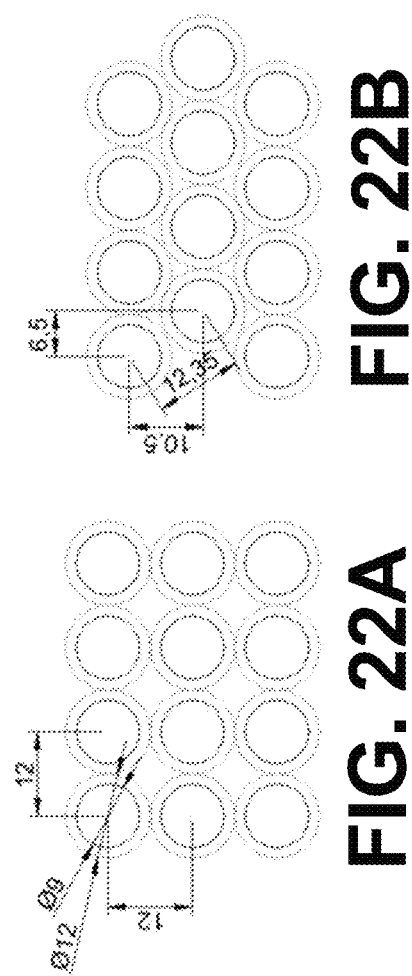

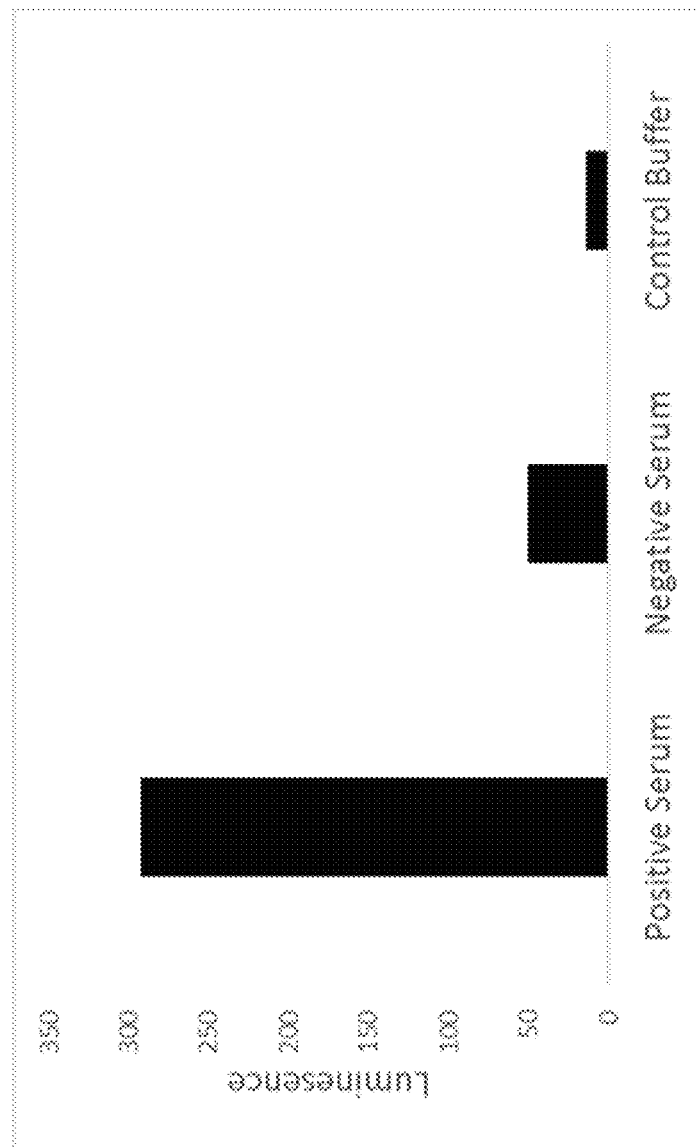

Treated

Non-treated

DISPOSABLE BIOASSAY CARTRIDGE AND METHOD OF PERFORMING MULTIPLE ASSAY STEPS AND FLUID TRANSFER WITHIN THE CARTRIDGE

FIELD

The present disclosure relates to a disposable cartridge and method to move fluids and carry out multiple bioassay steps within the cartridge that simplifies the design and removes the need for any internal valves or metering devices. The design is amenable to injection molded manufacturing lowering cost for large volume manufacturing.

BACKGROUND

Typical cartridge devices for biological assays are interfaced with an instrument containing syringes or other types of positive displacement pumps in order to accurately meter liquid volumes required sequentially in a reaction zone within the disposable cartridge. This often also involves the integration of mechanical valves within the cartridge structure to control fluid flows. In addition, care must be taken in the design of the fluidic paths to eliminate the formation of air bubbles that can significantly interfere with accurate fluid transfer. Complex structures or bubble control mechanisms are introduced into the design to mitigate these issues. This introduces manufacturing complexity and increased cost of the cartridges which are often meant to be used in a disposable fashion.

In view the trend toward point of use diagnostic testing, there is a need to integrate multiple functions/assay steps in a single cartridge on a cost effective basis consistent with mass production of the disposable cartridges. Therefore, it would be very beneficial to provide a disposable cartridge which integrates multiple functions with a minimum number of moving parts such as active pumps and valves in the field of automated point of use diagnostic bioassays.

SUMMARY

The present invention is directed to device and method to transfer liquid volumes sequentially to a reaction zone with only the use of applied pressure or vacuum and does not require any internal valves. Fluidic transfer is limited within the cartridge by capillary pressures. Flow between reaction zones may be effected by switching pressure or vacuum between ports with external valves and hence selectively exceeding the capillary pressure in the elements of the cartridge connecting reaction zones. The pressure/vacuum source and valves are located in the instrument itself and are isolated from reaction fluids. None of these components are part of the disposable cartridge, significantly lowering complexity and cost.

In an embodiment there is provided a disposable sample handling cartridge for performing multiplex biological assays, comprising:

a) an upper processing chamber having a preselected volume and having a pneumatic port mounted on a top of the upper processing chamber;

b) a lower processing chamber located below said upper processing chamber and having a pneumatic port mounted on a top of the lower processing chamber;

c) a microporous substrate positioned to separate the upper processing chamber from the bottom processing chamber with the microporous substrate forming the bottom of the upper processing chamber wherein the microporous substrate is connected to a body of the upper processing chamber in such a way that fluids can only exit through the bottom of the upper processing chamber into lower processing chamber by passing through the microporous substrate when an applied pressure differential across the microporous substrate exceeds a critical pressure;

d) one or more reagent reservoirs being in flow communication with said upper processing chamber by capillary channels configured to terminate in a top of the upper processing chamber such that they are located above a level of liquid in the upper processing chamber while performing assays, each reagent reservoir including at least one pneumatic port located on a top of the reservoir, a volume of the upper processing chamber being selected to be greater than a liquid volume to provide a head space in an upper portion of the upper processing chamber into which the capillary channels terminate;

e) an additional chamber in flow communication with said lower processing chamber by a capillary channel terminating in a top of the additional chamber, said addition chamber including a pneumatic port mounted on a top of the additional chamber; and wherein transport of liquids between selected chambers are controlled by application of pneumatic pressures with magnitudes required to overcome capillary pressure resistance between chambers.

In an embodiment there is provided a method for a performing biological assay, comprising:

providing a disposable sample handling cartridge having at least one set of processing chambers with each set of processing chambers including an upper processing chamber and a lower processing chamber separated by a microporous substrate, the porous substrate being constructed of material containing pores selected to provide a uniform resistance to flow across its entire surface such that at a defined pressure differential across the porous substrate, liquids will pass through the pores but gases will not, the microporous substrate having analyte specific receptors bound in said pores;

applying a differential pressure between one or more reagent chambers and a sample chamber containing an analyte and the upper processing chamber for moving liquids containing reagents and/or from one or more reagent chambers and sample chamber through capillary channels to the upper processing chamber;

applying a differential pressure between the upper processing chamber and the lower processing chamber for moving the liquids through the microporous substrate from the upper processing chamber to the lower processing chamber with the differential pressure being selected to force the liquid through the microporous substrate but not gas;

detecting for analytes bound to the analyte specific receptors on the microporous substrate; and applying a differential pressure between the lower processing chamber and a waste chamber for moving liquids from the lower processing chamber to the waste chamber.

The present disclosure provides a microporous substrate for detection of surface bound substances, comprising:

a generally planar microporous substrate material having opposed surfaces and pores extending through a thickness of said microporous substrate in which the pores are wider near one surface of the microporous substrate compared to a width of the pores on the opposed surface thereby improving the collection efficiency of light emitted from optical probes bound to the interior surfaces of the widened pores.

The pores may be progressively wider near one surface of the microporous substrate.

The device, method disclosed herein is of particular use in the area of medical diagnostics (human and veterinary), food safety testing, monitoring of environmental and biological hazards and general measurement of biological species. The design can be adapted to carry out most common assay formats for both proteins and nucleic acids including sample preparation steps.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the drawings, in which:

FIGS. 11A to 11C show three (3) tapered pores with different angles of tapering. Smaller tapering angle (B compared to A) leads to deeper tapering. For small enough angles the tapering is continuous from one surface of the substrate to the other as shown in C.

FIG. 18 confirms the expected 40% improvement of light collection efficiency according to disclosure.

FIG. 22A shows a first embodiment of an arrangement of the tapered cylindrical pores in the microporous substrate.

FIG. 22B shows a second embodiment of tapered cylindrical pores in the microporous substrate being more closely packed than the arrangement of FIG. 22A with enhanced light collection efficiency.

FIG. 26 shows results of a protein bioassay conducted using the assembled cartridge shown in FIG. 7.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

Figure 1:
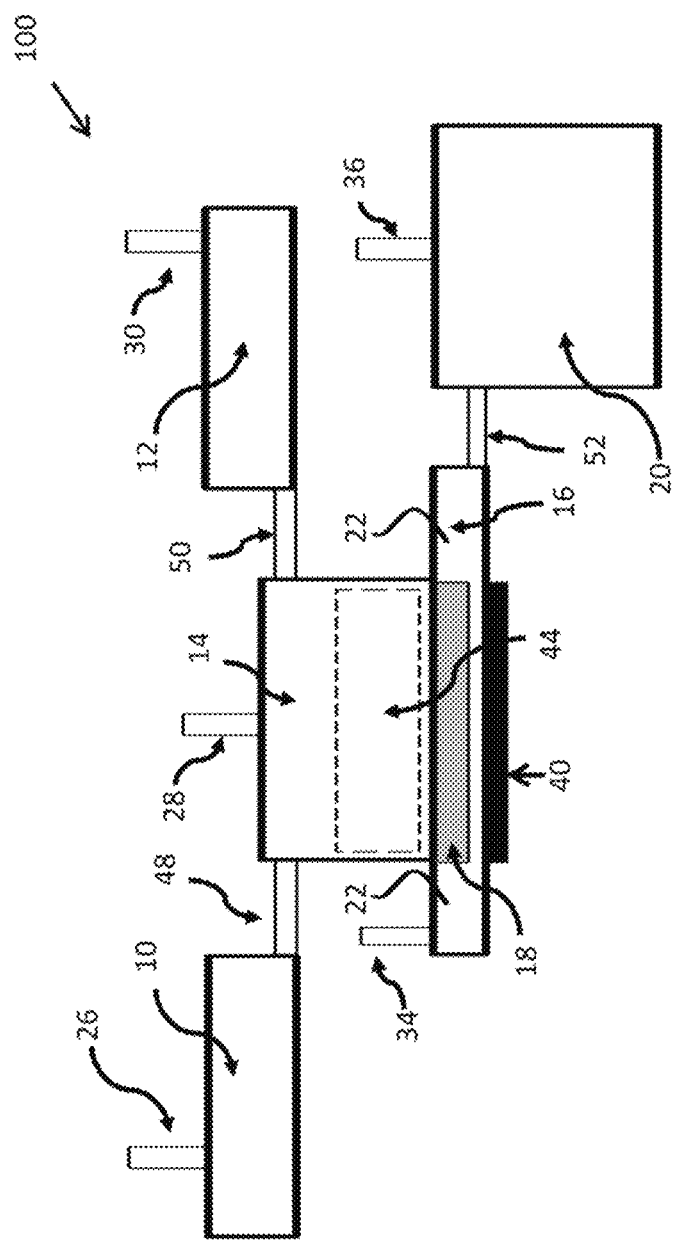
FIG. 1 is a side elevational view of a pneumatically driven assay cartridge showing the core components.

Referring to FIG. 1, there is shown a cartridge 100 configured to facilitate movement of fluids without the need for any internal valves or metering devices. The design is amenable to injection molded manufacturing lowering cost for large volume manufacturing. Cartridge 100 includes a first reagent chamber 10 which holds a liquid reagent or sample, and a second reagent chamber 12 which holds a second liquid reagent.

An upper processing chamber 14 is provided having a volume greater than first reagent chamber 10 or second reagent chamber 12. Cartridge 100 includes a lower processing chamber 16 which has a volume equal to or exceeding the maximum liquid capacity of upper processing chamber 14 and is designed to minimize the space between the bottom inner surface of chamber 16 and the bottom surface of a microporous substrate 18 located within chamber 16. Cartridge 100 includes an outlet chamber 20 with a volume greater than all of the reagents and samples combined.

First reaction chamber 10 includes a pneumatic port 26 which is configured to provide negative differential pressure, positive differential pressure or vent under external system control to chamber 10. Upper processing chamber 14 includes a pneumatic port 28 which is configured to provide negative differential pressure, positive differential pressure or vent under external system control to upper processing chamber 14. Second reaction chamber 12 includes a pneumatic port 30 which is configured to provide negative differential pressure, positive differential pressure or vent under external system control to chamber 12. Lower processing chamber 16 includes a pneumatic port 34 which is configured to provide negative differential pressure, positive differential pressure or vent under external system control to lower processing chamber 16. Similarly, outlet chamber 20 includes a pneumatic port 36 configured to provide negative differential pressure, positive differential pressure or vent under external system control to outlet chamber 20.

Pneumatic ports 26, 28, 30, 34 and 36 may incorporate flexible diaphragms in their respective pneumatic conduits which can be used to isolate a given chamber from a pneumatic source while allowing a flux of gas through the conduit which is limited by the deformation of the diaphragm. Upon application of pneumatic pressure, gas will flow through the conduit until the back-pressure of the diaphragm equals the applied pneumatic pressure. Such flexible diaphragms are disclosed in U.S. Pat. No. 7,470,546, which is incorporated herein by reference in its entirety.

More particularly, flexible diaphragms may be incorporated into pneumatic ports 28 and 34 in FIG. 1 so that when a positive pneumatic pressure is applied to port 28 gas flows into upper processing chamber 14 until the diaphragm deforms enough to create a back pressure equal to the applied pressure. The gas entering the upper processing chamber 14 causes the liquid to flow through the microporous substrate 18 into lower processing chamber 16, and air flows through port 34 and deforms the diaphragm in port 34 which would be vented to the atmosphere. Although port 34 is vented to the atmosphere there would be no passage of material between the interior of the cartridge 100 and the environment. This configuration permits back-and-forth transport of liquid across the microporous substrate 18 by the periodic application of pressure to port 28 which can be vented to the atmosphere when pressure is not applied.

The microporous substrate 18 serves as an interface between processing chambers 14 and 16 and has a size and shape configured to prevent fluid from passing between processing chambers 14 and 16 other than through the microporous substrate 18 when the critical pressure is exceeded. Head spaces 22 are produced in lower processing chamber 16 due to microporous substrate 18 projecting into lower processing chamber 16. While FIG. 1 shows two (2) head spaces 22 it will be understood that the cartridge may be configured to have only one. The direction of flow depends on the sign of the differential pressure between chambers 14 and 16.

Lower processing chamber 16 includes an optical window 40 which forms part of the lower surface of this lower processing chamber 16 to allow imaging of the microporous substrate 18 from outside the device cartridge 100. In those embodiments using microporous substrate 18 which has been functionalized with binding agents and which imaging is to be performed through optical window 40, microporous substrate 18 is a rigid substrate disposed in a rigid plane parallel to the image plane of the imaging device such that it does not move or is not displaced which would result in poor quality images being detected. Preferred properties and structure of rigid microporous substrate 18 will be discussed hereinafter.

Upper process chamber 14 includes a solid support zone 44 which is the space immediately above the microporous substrate 18 which can be occupied by a solid support material of a larger size than the pores in the microporous substrate 18 such that the material is retained in zone 44 since it cannot pass through the microporous substrate 18. The support material is capable of binding analytes of interest or acting as a support for reactions between bound and soluble materials.

A capillary flow channel 48 connects reagent chamber 10 with the upper processing chamber 14 and is designed with an inner diameter sized to prevent flow in either direction until a differential pressure is applied exceeding a preselected critical level to permit flow between the chambers 10 and 14. A capillary flow channel 50 connects reagent chamber 12 with the upper processing chamber 14 and is designed with an inner diameter sized to prevent flow in either direction until a preselected differential pressure is applied exceeding the critical level to permit flow between the chambers 12 and 14. A capillary flow channel 52 connects lower processing chamber 16 with the outlet chamber 20 and is designed with an inner diameter sized to prevent flow in either direction until a preselected differential pressure is applied exceeding the critical level to permit flow. For example, the capillary inner diameter could be selected from the range of 50 to 500 microns to provide critical pressures of 0.1 to 0.5 psi.

Flow is effected from one chamber to the next by applying pressure to the originating chamber containing the fluid through the pneumatic port mounted on that chamber while simultaneously venting the destination chamber to which the capillary channel is connected through the pneumatic port mounted on that chamber. Alternatively, negative differential pressure can be applied to the destination chamber while simultaneously venting the originating chamber. In both cases a sufficient pressure differential must be provided to overcome the resistance of the channel and allow flow to occur.

In the case when a cycling of the fluid is required between two reagent chambers (e.g. for mixing) the differential pressure between these chambers can be changed from positive to negative and back to positive. This will change the direction of fluid flow.

Reagent chambers 10 and 12 may contain liquid reagents or dried reagents for dissolution in the device by transferring a solution from another chamber. One or more of the reagent chambers 10 and 12 may be designed to accept the introduction of a sample or other material from an external source. It is noted that while only two (2) reagent chambers 10 and 12 are shown connected to upper processing chamber 14, more could be included depending on the application at hand. Each reagent chamber 10 and 12 is provided with the port 26 for chamber 10 and port 30 for chamber 12 which can be interfaced with an external pneumatic system capable of providing one or more of positive or negative pressures or venting to a given chamber under external control.

The upper processing chamber 14 is provided with port 28 which can also be interfaced with an external pneumatic system capable of providing one or more of positive or negative pressures or venting to the chamber under external control.

The internal diameter of each capillary channel 48, 50 and 52 is selected to only permit flow through the channel from one chamber to the other when a differential pressure exceeding the critical pressure is applied. The length of the of the channel may be designed in the range of 5 to 30 mm in combination with the selected inner diameter in order to control the time required to transfer the full reagent volume between chambers in 1 to 60 seconds using applied pressures in the range of 0.1 to 1.5 psi. The internal diameter of each capillary channel 48, 50 and 52 can be constant along the channel. Alternatively, a part of the channel 48, 50 and 52 may have a smaller diameter (e.g. 50-500 um) and the rest of the channel may have a larger diameter (e.g. 500 um-2 mm). This type of channels 48, 50 and 52 allow independent selection of the critical pressure and flow rate.

The upper processing chamber 14 is sized to exceed the total volume of reagents or sample fluids that may be transferred to the upper processing chamber 14 at any time. As seen in FIG. 1, capillary channel 48 connecting reagent chamber 10 to upper processing chamber 14 and capillary channel 50 connecting reagent chamber 12 to upper processing chamber 14 are positioned so that they terminate in the upper portion of the upper processing chamber 14 such that all are above the maximum level of liquid reached in the chamber. The bottom of the upper processing chamber 14 is composed of the microporous substrate 18 connected to the body of the chamber 14 in such a way that fluids can only exit through the bottom of the chamber 14 by passing through the microporous substrate 18 when the differential pressure exceeds the critical pressure.

The upper processing chamber 14 may also contain the solid support 44 in the form of beads, particles, gels, or other similar materials that are capable of binding materials of interest from fluids within the chamber or acting as a support for bound materials to interact with materials contained in the fluid. These solid support materials 44 are of sufficient size that they are retained by the microporous substrate 18 and do not restrict flow through the substrate 18.

The microporous substrate 18 may also be composed of a material or modified in such a way as to act as a solid support capable of binding materials of interest from fluids that pass between the upper processing chamber 14 and the lower processing chamber 16 or acting as a support for bound materials to interact with materials contained in the fluid.

The microporous substrate 18 is constructed of material containing pores selected to provide a uniform resistance to flow across its entire surface such that at a defined pressure differential across the substrate 18, fluids will pass through the pores but gases (e.g., air) will not. The properties of the pores are selected such that the resistance to flow will not be overcome by the weight of liquids in the upper processing chamber 14 or allow capillary action to draw fluids completely through the pores in substrate 18. The properties of the microporous substrate 18 may optionally be selected to require a pressure differential to initiate flow that is in the same range as that required to initiate flow through capillaries 48, 50 and 52 in order to simplify design of the external pneumatic system. Flow between the upper processing chamber 14 and the lower processing chamber 16 is effected by applying pressure to the upper processing chamber 14 containing the fluid while simultaneously venting the lower processing chamber 16 separated by the microporous substrate 18.

Alternatively, negative pressure can be applied to the lower chamber 16 while simultaneously venting the upper chamber 14. In both cases the pressure differential must be provided in a range that is sufficient to overcome the resistance of the pores in the substrate 18 and allow flow of liquids to occur but below that required to overcome the resistance to the flow of air through the pores. The process may be reversed to effect flow in the opposite direction to allow repeated contact with the substrate 18 and any solid support 44 contained in the upper chamber 14 as well as to provide efficient mixing.

The lower processing chamber 16 is provided with two or more ports 34 (only one is shown in FIG. 1) which can be interfaced with an external pneumatic system capable of providing one or more of positive or negative pressures or venting to the chamber 16 under external control. The lower processing chamber 16 has a volume equal to or greater than the maximum volume of reagents or sample fluids that may be transferred from the chamber 16 at any time.

The base of the lower processing chamber 16 is positioned in close proximity to the lower surface of the microporous substrate 18 while additional volume can be provided by extending a portion of the chamber 16 above the outer walls of the upper processing chamber 14 to form a headspace 22.

The lower surface of the lower processing chamber 16 which includes the optically transparent window 40 which allows for imaging of the lower surface of the microporous substrate 18 using for example a charge coupled device (CCD) camera or other suitable optical sensor.

The lower processing chamber 16 is connected to one or more outlet chambers 20 by one or more capillary channels 52 extending from the lowest point of the lower processing chamber 16 and terminating in the upper section of the outlet chamber 20 at a point above the maximum level of liquid to be contained in the outlet chamber 20. At least one of these capillary channels 52 is positioned at the lowest level of the chamber 16 to allow substantially all of the liquid in the chamber 16 to be removed through channel 52.

One outlet chamber 20 may be used for waste containment in which case it is sized with a volume greater Than the sum of all the fluids that need to be transferred from the lower processing chamber 16. Another outlet chamber (not shown) may be used to transfer fluids to additional downstream chambers for further processing, depending on the tests to be performed.

In addition to controlling the flow of the fluid, the microporous substrate 18 alone or in combination with the solid support 44 may be used to bind components in the fluid, and the bound components may be separated from the bulk fluid, washed, modified or copied, serve as binding agents for additional components, recovered for further use or any combination of these steps by the sequential transport of at least one fluid from a chamber on the device.

In addition to controlling the flow of the fluid, the microporous substrate 18 may be designed to bind different substances in the fluid at different regions of the substrate 18, substances bound at different regions of the substrate 18 are subsequently detected and/or quantified.

A single device 100 may contain one or more processing zones (two are shown as processing chambers 14 and 16 but more could be included) which uses it's integral microporous substrate 18 to accomplish different functions including analyte capture (nucleic acid, protein, small molecule other biological or chemical entities), modification of captured analyte (replication, extension, amplification, labeling, cleavage, hydrolysis), modification of soluble analytes through immobilized enzymes or catalysts, retention of solid matrix for higher capacity capture (beads, particles, gels), detection and/or quantitation of one or more captured analytes through optical imaging (colorimetric, fluorescent, chemiluminescent, bioluminescent). In all cases the microporous substrate 18 also acts as a fluid control device necessary to carry out these functions.

The side views of FIGS. 2 to 6 show side views of an actual cartridge produced using plastic in which a central plastic cartridge reagent plate 82 is sandwiched between an upper cartridge plate 80 and a lower cartridge plate 84. FIG. 7 shows a photograph of an assembled cartridge and FIGS. 2 to 6 may be considered cross sections taken from FIG. 7.

Figure 2:
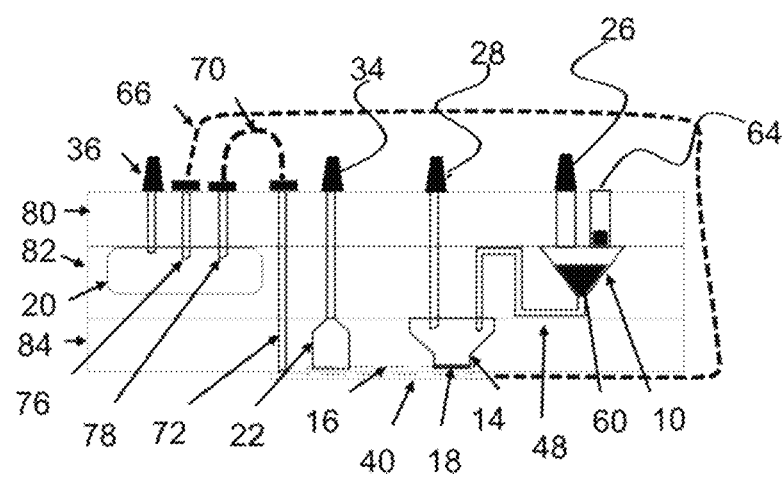
FIG. 2 shows a more detailed side view of the cartridge of FIG. 1 with liquids in the starting position.
Figure 3:
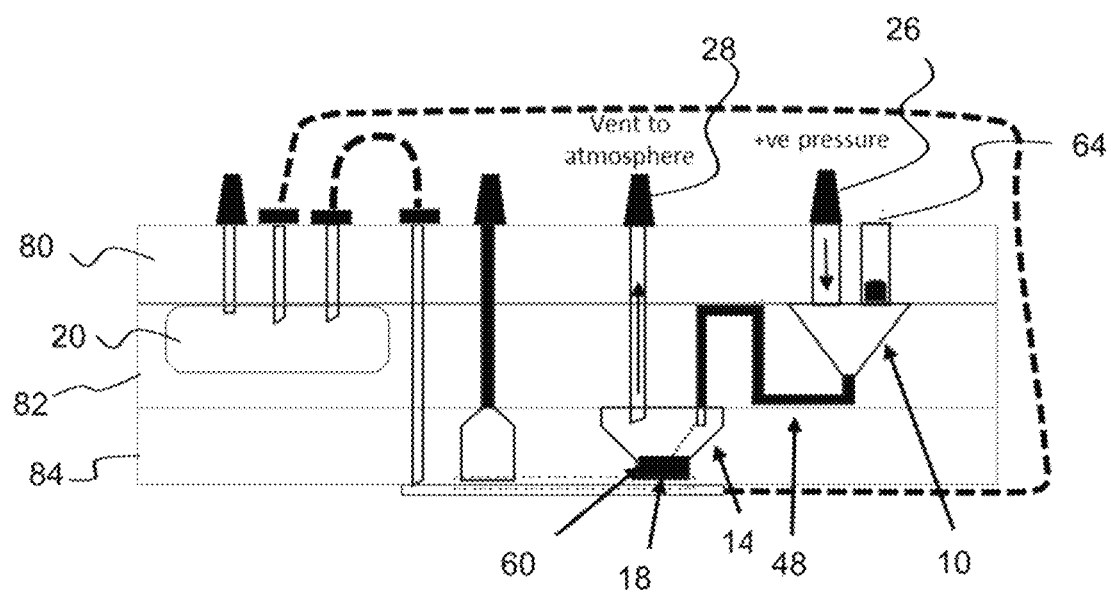
FIG. 3 is an enlarged view of the side view of FIG. 2 showing movement of the liquid (thick dark line within the capillary) from a reagent reservoir to an upper processing chamber under pneumatic control.

FIGS. 2 and 3 illustrate the dispensing of a liquid reagent or sample into the upper processing chamber 14. The liquid reagent or sample 60 is loaded into the reagent chamber 10 prior to the assay through a reagent/sample entry port 64 and then the port 64 is closed. A pressure of ~1 psi is applied to the chamber 10 containing the liquid 60 via port 26 while port 28 connected to the upper processing chamber 14 is vented creating a pressure differential allowing the reagent to flow through the reagent capillary channel 48 into upper processing chamber 14. The liquid 60 falls to the bottom of the upper processing chamber 14 and covers the integral microporous substrate 18. Any excess air is allowed to vent through port 28. This method of dispensing fluids is similar for all other reagent chambers used in the assay, with the exception of a bulk wash buffer (not shown) which is stored in a larger reservoir and metered through a capillary channel on a timed basis so that a precise volume can be delivered during dispensing.

Figure 4:
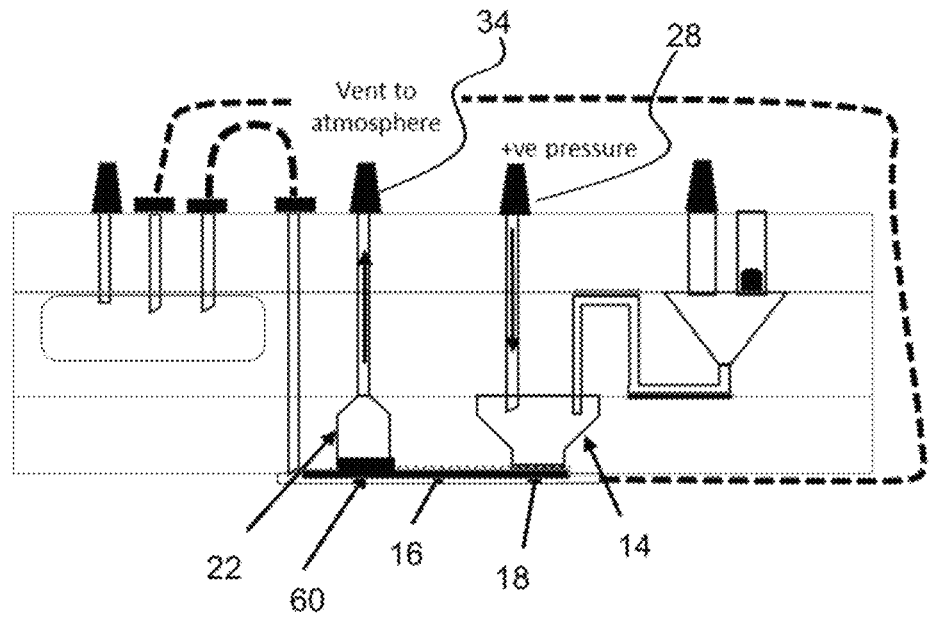
FIG. 4 is similar to FIG. 3 showing movement of the liquid from the upper processing chamber to a lower processing chamber through a microporous substrate under pneumatic control.

Referring to FIG. 4, to pull the fluid through the microporous substrate 18, a differential pressure is created by applying pressure through port 28, while venting to atmosphere through port 34. All other ports are closed during cycling. Fluid 60 travels from the upper processing chamber 14 into the lower process chamber 16 and headspace 22. By applying a pressure differential above the critical pressure for liquid flow through the microporous substrate 18 while not exceeding the critical pressure required for air flow through the microporous substrate 18, flow continues until all liquid 60 is drawn from the upper processing chamber 14 and then stops. This design ensures that no air is drawn through, eliminating any bubbles that might interfere with processing or operation of the cartridge.

Figure 5:
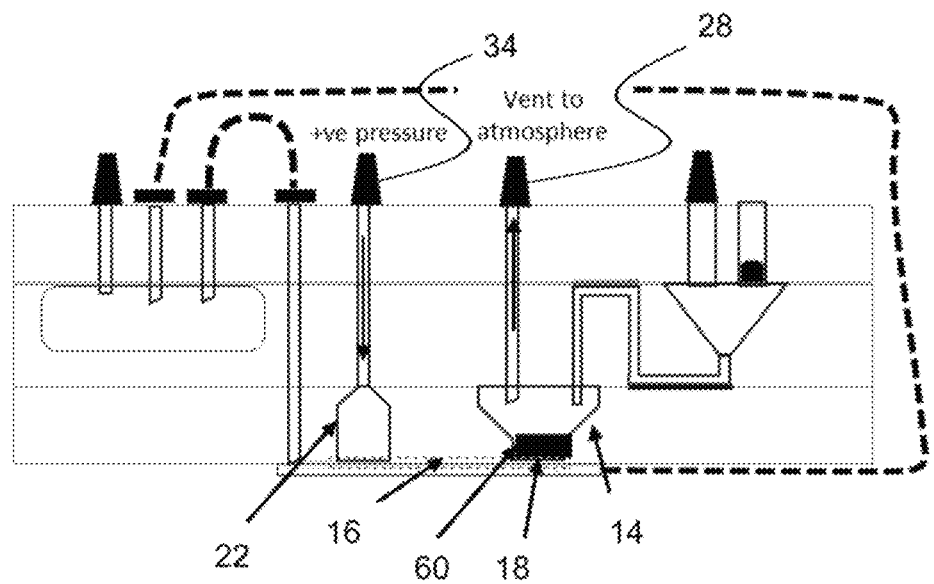
FIG. 5 shows the liquid in the cartridge being moved back into the upper processing chamber under pneumatic control.

Referring to FIG. 5, to provide repeated contact with microporous substrate 18 alone or in combination with the solid support 44 and to ensure efficient mixing, fluid 60 may be returned to the upper processing chamber 14 by reversing the process. A differential pressure is created by applying pressure to port 34 while simultaneously venting to atmosphere through port 28. By applying a pressure differential above the critical pressure for liquid flow through the microporous substrate 18 while not exceeding the critical pressure required for air flow through the microporous substrate 18, flow continues until all liquid 60 is drawn from the lower processing chamber 16 back up to upper chamber 14 and then stops. This principle eliminates the need for any precise volumetric control of fluid flow and greatly simplifies control. The process of cycling back and forth through the substrate 18 can be repeated as many times as required.

Figure 6A:
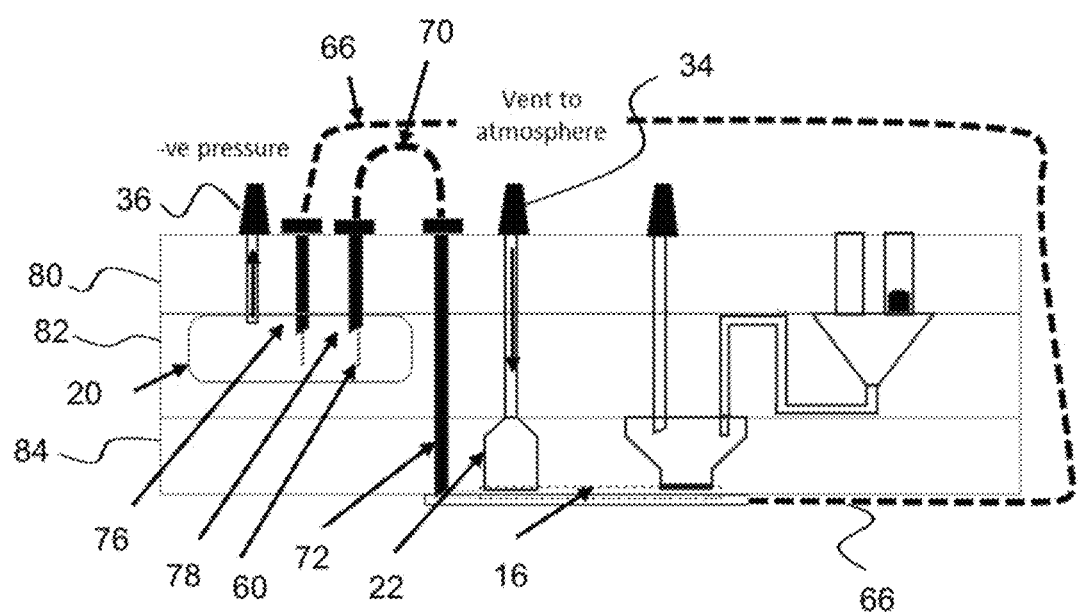
FIG. 6A shows the liquid in the cartridge partially moved into a waste container after completion of the processing steps.
Figure 7:
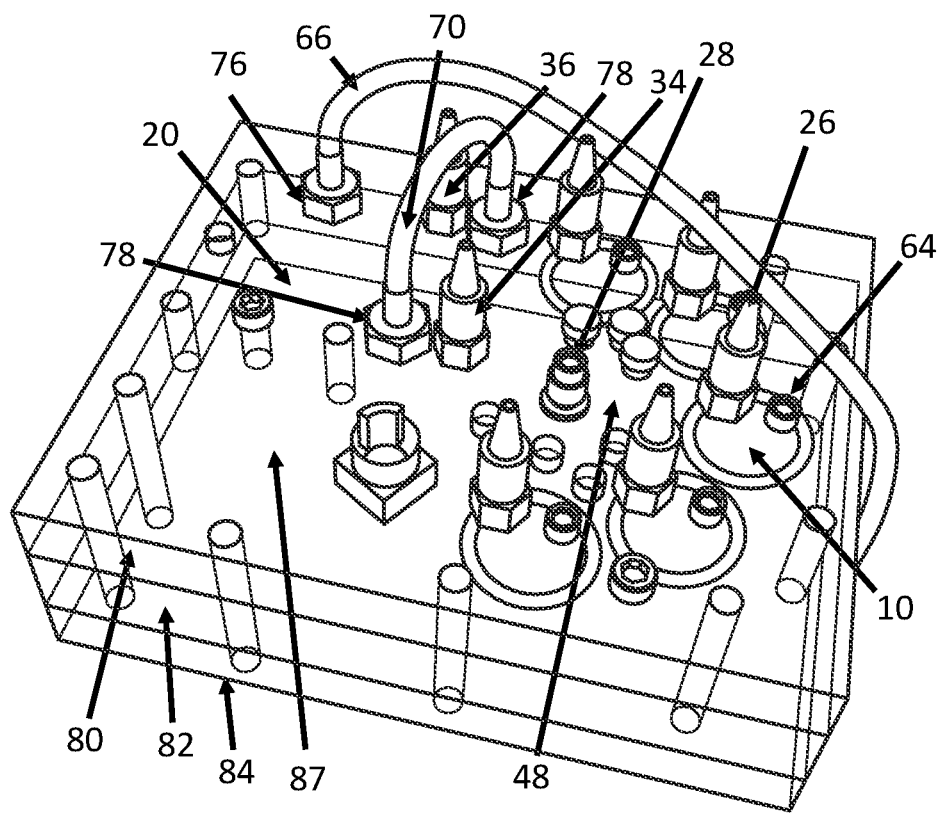
FIG. 7 is a photograph of an assembled cartridge showing five (5) reagent/sample chambers and a bulk reagent chamber connected to a central upper processing chamber.

Referring to FIG. 6A, evacuation of the fluid from the lower processing chamber 16 is effected by applying a negative pressure through port 36 on chamber 20 while venting to atmosphere through port 34. This allows air to enter through the lower processing chamber 16 headspace 22 and liquid 60 to travel though a distal waste capillary channel 66 from one side of lower chamber 16 coupled to a waste inlet 76 which empties into chamber 20 and a proximal waste capillary 70 coupled to a proximal waste outlet 72 exiting from the other side of chamber 16 coupled to a waste outlet 78 which empties liquid 60 into chamber 20.

Figure 6B:
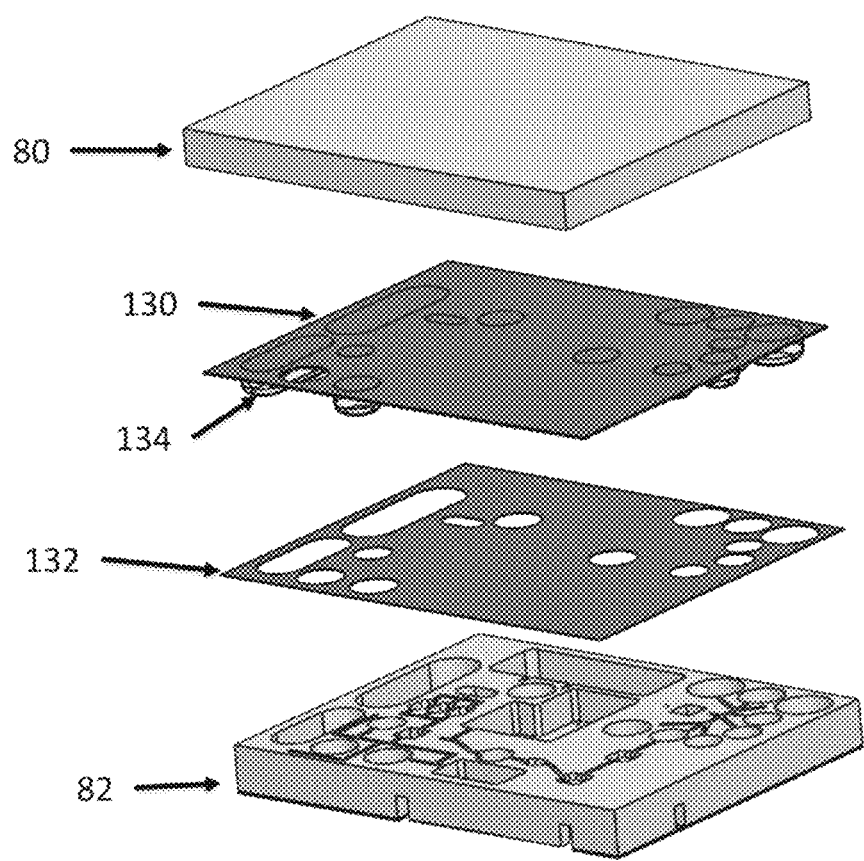
FIG. 6B shows a kit including a disposable cartridge along with a dedicated blister pack containing a plurality of assay reagents and a matching gasket with the packets containing the assay reagents being aligned with preselected reagent chambers.

FIG. 6B shows an embodiment which is a kit including a disposable cartridge 100 along with a dedicated blister pack 130 containing a plurality of packets 134 containing selected liquid assay reagents and a matching gasket 132 with the packets 134 containing the assay reagents being aligned with preselected reagent chambers in plastic cartridge reagent plate 82. The assembled cartridge 100 with upper cartridge plate 80 includes the packets 134 partially projecting into their corresponding reagent chambers. When inserted into the instrument to implement the biological assay, applying pressure via the pneumatic system coupled to the pneumatic ports on plate 80 (not shown) of the various chambers results in rupturing of frangible seals in the blister pack resulting in the reagents flowing into their respective chambers. The gasket 132 provides a liquid and gas seal between chambers. Additional solid reagents may be deposited into preselected reagent chambers within plastic cartridge reagent plate 82 prior to assembly of cartridge 100, providing flexibility in the customization of reagent selection for desired biological assays and simplifying storage and transport requirements.

As noted above, FIG. 7 is a photograph of an assembled cartridge showing five (5) reagent/sample chambers 10 connected to a central upper processing chamber 14. This photograph shows the cartridge without the pneumatic connection to the cartridge. A nucleic acid bioassay (FIG. 25) and a protein bioassay (FIG. 26) were conducted using the assembled cartridge shown in FIG. 7.

Analysis of nucleic acids usually requires processing steps to isolate nucleic acids and to derive labelled copies of them for subsequent detection. Many applications require the analysis of many different target sequences, and high analytical sensitivity is often required. Furthermore, automated, cost-effective systems will be required so that relatively unskilled people will be able to perform the tests reliably for routine clinical testing.

Purification and amplification of multiple nucleic acids targets can be performed by capturing the nucleic acids on a solid support and performing a series of incubation and washing steps on the support to produce derivatives of the nucleic acids that can be analyzed by hybridization on nucleic acid probes arrayed on the microporous substrate.

Figure 8:
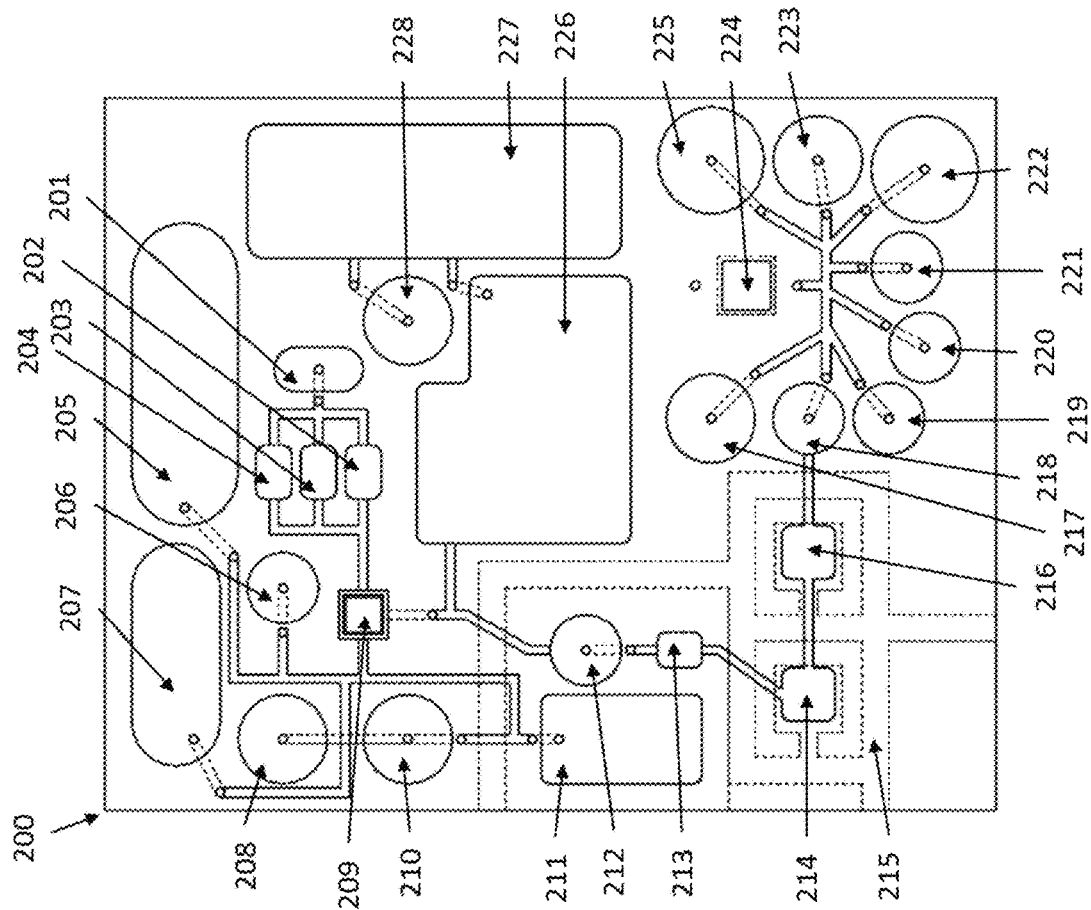
FIG. 8 shows a top view of a cartridge configured for both nucleic acid sample preparation and nucleic acid amplification (isothermal or polymerase chain reaction (PCR)) and multiplex detection of the products.

FIG. 8 and its included legend shows a top view of a configuration of a bioassay cartridge 200 which incorporates design of cartridge 100 but is configured for both nucleic acid sample preparation and nucleic acid amplification (isothermal or polymerase chain reaction (PCR)) and multiplex detection of the products. Cartridge 200 is configured for both sample preparation using one microporous support 18 in processing chamber 209 and reaction product detection using a second porous substrate 18 in processing chamber 224 each consisting of an upper processing chamber 14 and a lower processing chamber 16 separated by microporous substrate 18.

Cartridge 200 provides for a sample inlet 208, a means to mix the sample with a lysis or pretreatment buffer 210, a processing chamber 209 containing microporous substrate 18 in which capture and modification of nucleic acids from the sample can be performed using dried or liquid reagents supplied from chambers 205, 207, 201, 202, 203, 204, or 206. Fluids from the processing chamber 209 may be transferred to waste chamber 226 or in the case of fluid containing the derivative nucleic acids to a thermal treatment chamber 211 or intermediate chamber 212.

Figure 9:
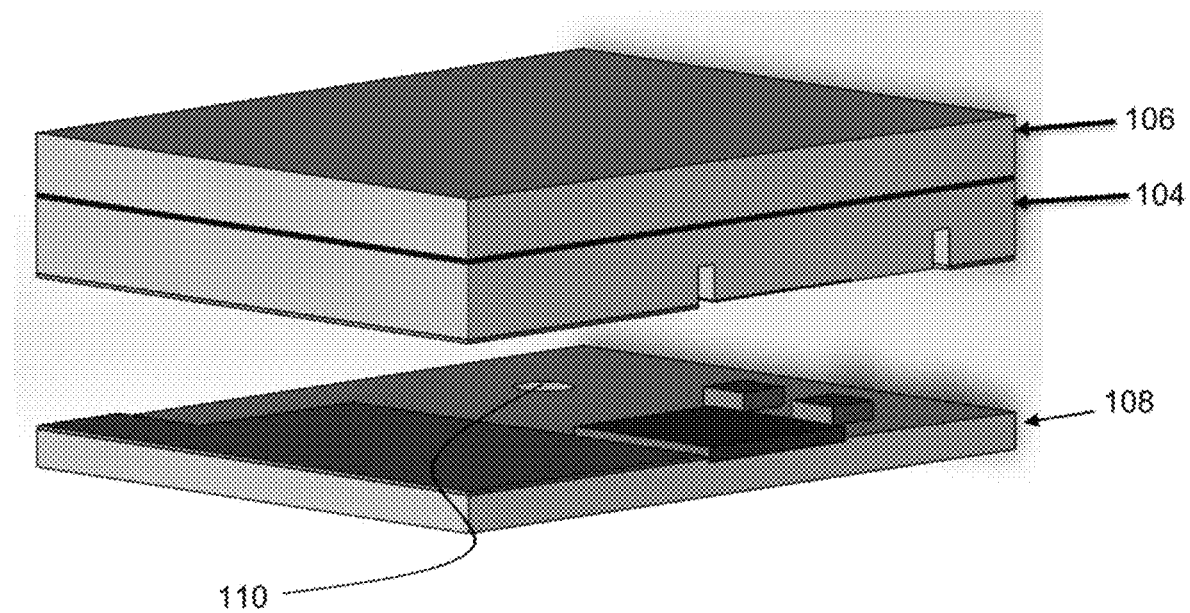
FIG. 9 shows a partially disassembled view of the disposable cartridge sandwiched between an upper pneumatic block assembly interface and a lower thermal control assembly which form part of the instrument into which the cartridge is inserted.

Chamber 212 may be used to mix the fluid with dried or liquid reagent in chamber 213. Subsequently, the fluid may be processed through one or more temperature treatment chambers 214, 216 where isothermal or thermal cycling amplification may take place. These thermal treatment chambers 211, 214, 216 are isolated from the bulk of the cartridge by thermal insulating zones 215 and controlled by the application of heat or cooling from an external thermal control assembly 108 (FIG. 9). The processed liquid containing the amplified derivative nucleic acids can then be transferred to an intermediate chamber 218, mixed with an appropriate binding buffer 219 for hybridization to the microporous substrate 18, located in sample processing chamber 224 where the derivative nucleic acids are detected on bound nucleic acid probes immobilized in specific locations on the microporous substrate 18.

A series of steps as previously described are carried out using reagents from adjacent chambers 217, 220, 222, 223, 225 with spent fluids being directed to waste chamber 227. In all cases pneumatic pressure applied through ports located on each chamber is used to control fluid movement. As a final step, an image of the microporous substrate 18 is captured with a CCD camera with integral lens 120 (FIG. 10) located below the optical window 40 (FIG. 1). This image is analyzed for intensity of light measured across the microporous substrate and correlated to the specific regions known to contain the immobilized probes. This information is used to calculate the presence or absence or quantity of specific nucleic acids in the original sample.

Generally speaking, using the design principles disclosed above, cartridges may be configured to have multiple reagent/sample chambers/reservoirs, upper and lower processing chambers 14 and 16, and waste chambers 20. For example, waste chamber 20 may in fact be an intermediate chamber accepting reaction products from a first processing station including first and second upper and lower processing chambers 14 and 16 with chamber 20 forming a sample chamber for a second series of upper and lower processing chambers 14 and 16.

It will be understood that cartridge 200 may be configured with additional features to permit numerous intermediate processing steps to be carried out between the first and second set of upper and lower processing chambers 14 and 16. Non-limiting examples of these intermediate processing steps may include mixing, dilution, incubation, thermal treatment including but not limited to thermal cycling to give a few examples. Optionally cartridge 200 may include a decontamination chamber 228 containing a cleansing agent selected to destroy or neutralize harmful products of the assay or sample.

The system of FIG. 8 utilizing the disposable cartridge disclosed herein is very amenable to performing the above noted nucleic acid assay such as that disclosed in United States Patent Publication Serial No. US2018-0057855A1, which is incorporated herein by reference in its entirety, and which is a national phase entry patent application of PCT/2016/050367 filed on Mar. 29, 2016. Thus, the present disclosure provides a cartridge which in an embodiment comprises two different microporous substrates each with upper and processing chambers, one of which is a solid support for purification of multiple target nucleic acids and processing of the target nucleic acids to produce derivative nucleic acids, and the other of which is a porous substrate on which the derivative nucleic acids are detected on bound nucleic acid probes. The present cartridge, in conjunction with an instrument designed to operate it, will accept samples and provide clinically relevant information without user intervention after inserting the samples.

Analysis of proteins in biological samples (e.g., human serum) by immuno-binding reactions often requires dilution of the samples before the immuno-binding reactions. The present disclosure provides embodiments of a disposable cartridge comprising two different microporous substrates 18 each with associated upper and lower processing chambers 14 and 16, one of the coupled chambers 14 and 16 may be used for mixing of the sample with a diluent, and the second of the coupled chambers 14 and 16 includes a flow-through microporous substrate 18 on which the proteins are detected by immuno-binding reactions.

Specific volumes of the sample and of the diluent are transported to the upper processing chamber 14 above the first microporous support 18, and they are mixed by passing the solution through the porous substrate 18 into the lower processing chamber 16, and are pneumatically cycled or driven back and forth between the chambers 14 and 16 at least one time before the diluted samples are transported from the first lower processing chamber 16 to the second buffer processing chamber 14 above the second microporous substrate 18 for detection on the second microporous substrate 18. The first microporous substrate 18 may contain immobilized binding agents that would bind specific components in the sample. For example, interfering substances might be removed by binding to the first microporous substrate 18 before the immuno-binding step on the second porous substrate 18 is performed.

In another instance, low abundance substances may be concentrated from a large volume by binding to the first microporous substrate 18 and then being released in a smaller volume at higher concentration before the immunobinding step on the second microporous substrate 18 is performed in order to improve overall sensitivity of detection.

FIG. 9 shows a partially exploded view of the disposable cartridge 104 sandwiched between an upper pneumatic block assembly interface 106 and a lower thermal control assembly 108 which form part of the instrument into which the cartridge 104 is inserted. Pneumatic interface 106 includes all the requisite pneumatic coupling components, tubes and the like needed to couple to the pneumatic ports of the cartridge 104. All these components are housed in interface 106 and do not form part of the disposable cartridge 104.

Figure 10:
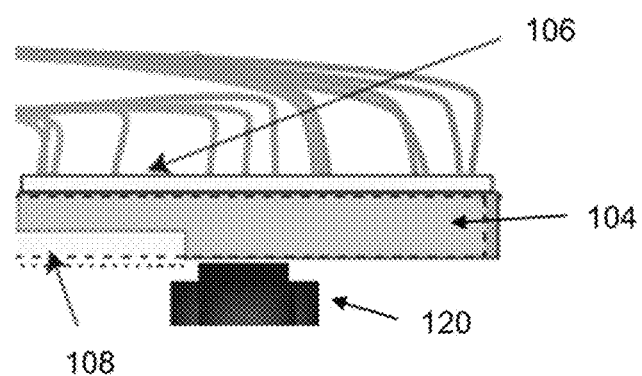
FIG. 10 is a partial cross sectional view of the sandwiched structure of FIG. 9 showing a detector positioned to view the microporous substrate.
Figure 12B:
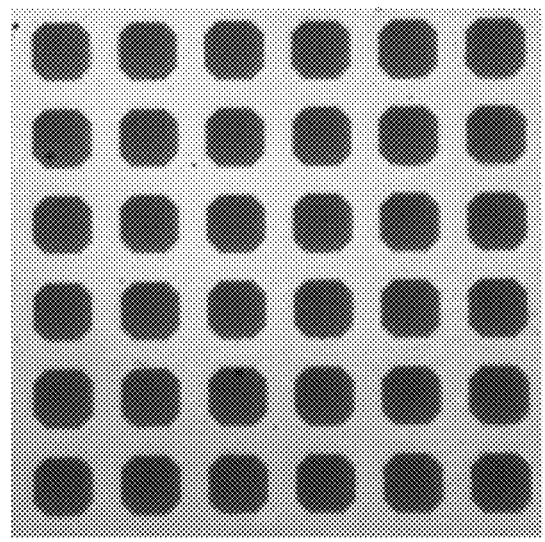
FIGS. 12A and 12B show optical microphotographs of the front and back surfaces of a silicon substrate with tapered pores according to the present disclosure. These optical micrographs show that the high porosity of the substrate on the side with widened pores (FIG. 12A) and the lower porosity of the substrate on the opposite side (FIG. 12B).
Figure 12A:
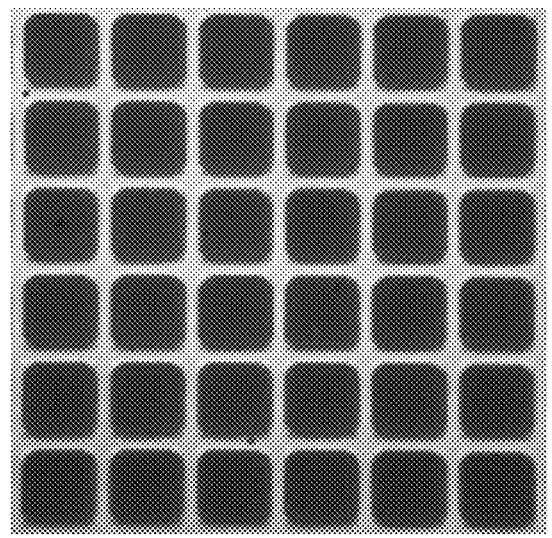

Similarly, thermal control assembly 108 contains all requisite features such as heaters, temperatures sensors and associated controllers, microprocessors and the like to control the temperature in selected zones of the cartridge 104. The thermal control assembly 108 includes a central aperture 110 which when assembled with cartridge 104 aligns with optical window 40 to allow imaging of the porous substrate 18. FIG. 10 is a partial cross sectional view of the sandwiched structure of FIG. 9 showing detector 120 positioned to view this microporous substrate 18 in the assembled system. Detector 120 which includes an appropriate objective lens is configured to image the bottom side of microporous substrate 18 to detect the presence of colorimetric, fluorescent, chemiluminescent, or bioluminescent signals.

A preferred material from which the microporous substrate 18 is produced is silicon which is rigid and opaque to chemiluminescent emission. This opacity prevents crosstalk between different pores of the substrate and hence prevents crosstalk between closely spaced regions on the substrate with different binding agents. This permits the analysis of many analytes in a small device, since different binding agents can be arranged in close proximity. As an example, the substrate may contain pores with a size in the range of 1 to 15 microns with wall thicknesses between pores ranging from 1 to 5 microns.

Referring to FIGS. 11A to 14C inclusive, in an embodiment of the microporous substrate 18, the two opposed sides have different pore sizes. The side of the substrate 18 from which light is collected to enable detection and analysis has substantially wider pores as can be seen in FIGS. 11A to 14C, and this side is the side facing into lower reaction chamber 16 and faces the optical window 40 from which the detector 120 (FIG. 10) is spaced. As can be appreciated from FIGS. 11A to C, the walls of the pores at this surface are tapered rather than being normal to the surface. This geometry presents a greater surface area to the detection optics and less restriction to the transmission of light from within the pores. Despite the large pores on a front surface and great porosity, the substrate 18 has adequate strength and structural stability for flow-through applications due to the small pore size on the opposite side and there is a substantial amount of material between the pores.

Figure 15B:
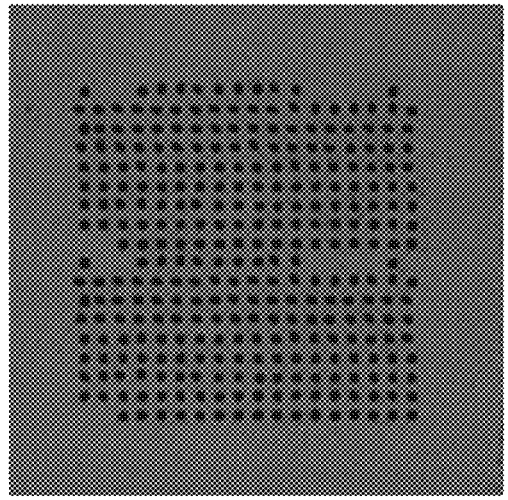
FIGS. 15A and 15B demonstrate the improvement in light transmission of a microporous substrate due to pore tapering. The same substrate is shown in FIGS. 15A and 15B when illuminated by the same diffuse light source. The widened part of the pores are facing the objective lens in FIG. 15A, and the narrow part of pores are facing the objective lens in FIG. 15B. The spots on the substrates are regions in which the pores of the substrate have been blocked with probe solutions that have dried in the pores.
Figure 15A:
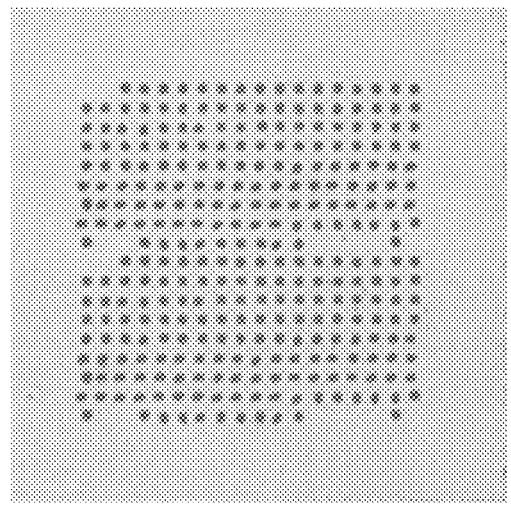

The remarkable asymmetric optical properties of the substrate are illustrated in FIGS. 15A and B. Specifically, FIGS. 15A and 15B demonstrate the improvement in light transmission of a porous substrate due to pore tapering. The same substrate is shown in 15A and 15B when illuminated by the same diffuse light source. The widened part of the pores are facing the objective lens in FIG. 15A and the narrow part of the pores are facing the objective lens in FIG. 15B. The spots on the substrates are regions in which the pores of the substrate have been blocked with probe solutions that have dried in the pores.

Figure 16C:
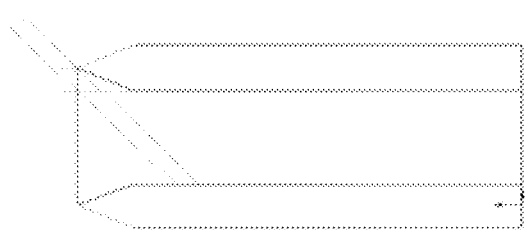
FIGS. 16A to 16C illustrate the mechanisms contributing to light collection improvement, with 16A showing the effect of increasing of the effective depth; 16B showing the effect of an increase in the collection angle; and 16C showing the effect of increase of surface area.
Figure 16B:
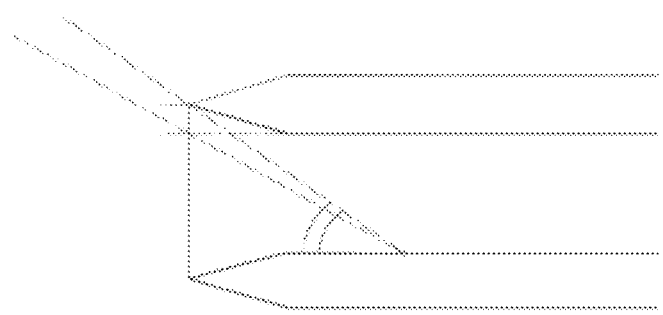
Figure 16A:
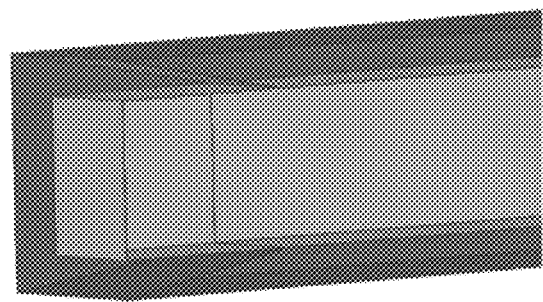

Tapering of the pore walls provides improvement of light collection due to increase of the depth from which the light can be collected, increase of the emitting surface area of the upper portion of a pore and increase of a collection angle. These mechanisms of light collection efficiency are illustrated in FIGS. 16A to 16C with 16A showing the effect of increasing the effective depth; 16B showing the effect of an increase in the collection angle; and 16C showing the effect of increase of surface area.

Figure 17:
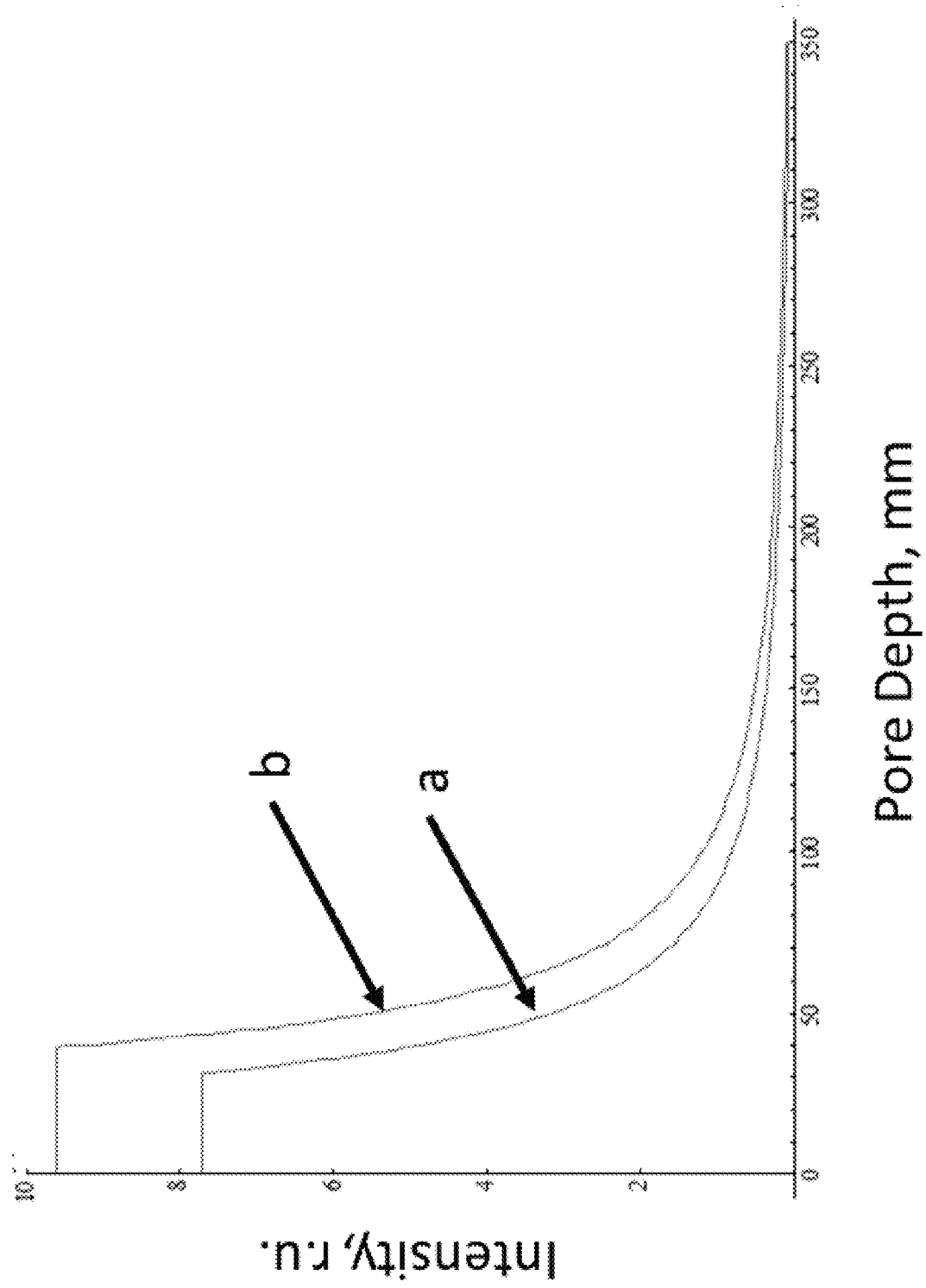
FIG. 17 shows the results of calculation of light collection efficiency as a function of pore depth for a straight 8 um (micrometers) pore (plot A) and a pore with tapered walls (plot B).

The results of the evaluation of these effects for a particular implementation of the method described in this application are shown in FIG. 17 which shows the results of calculation of light collection efficiency as a function of pore depth for a straight 8 um pore (plot A) and a pore with tapered walls (plot B). The parameters used for this evaluation are: 1) the width of non-tapered portion of a pore is 8 um; 2) the thickness of a wall between pores is 4 um; 3) the substrate thickness is 350 um; 4) tapering angle 2 degrees; 5) the diameter of the objective lens is 25.4 mm; and 6) the working distance of the objective lens is 50 mm.

In FIG. 17 the rise of the flat part of the curve is caused by increase of the collection surface area, the shift of the curve is caused by increase of the pore depth from which the light collection is limited by the parameters of the optical assembly rather than the pore walls, the change in a slope of the curve is associated with a change of the collection angle. As a result, the expected improvement of light collection efficiency is 1.4 to 1.5 fold.

Figure 18:
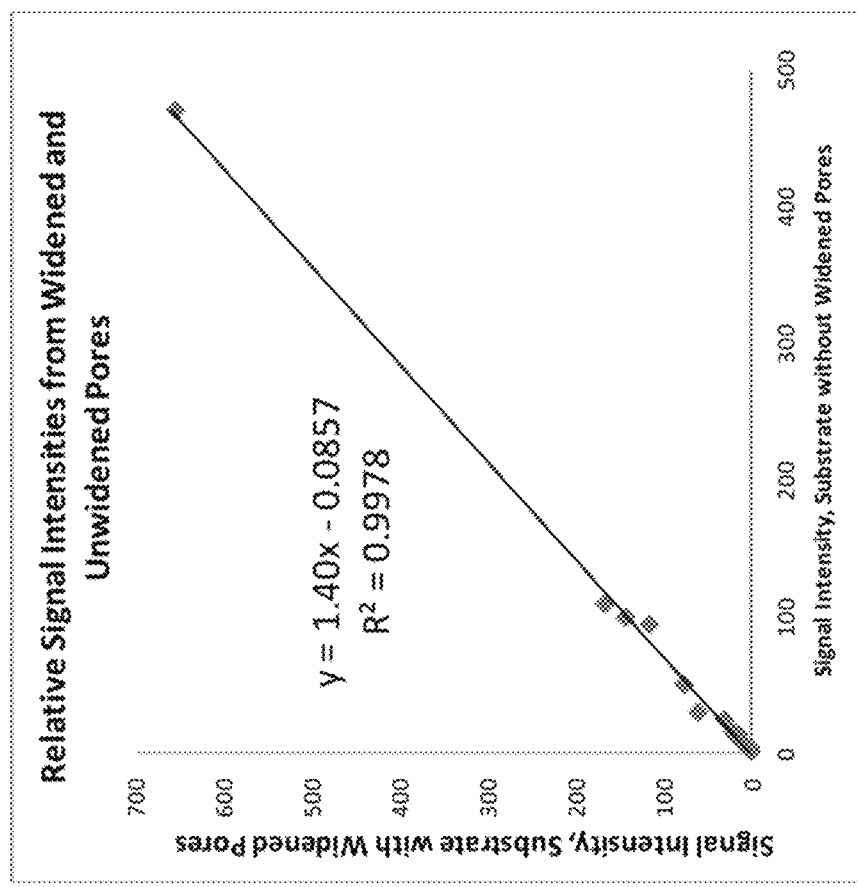
FIG. 18 shows the results of experimental comparison of signal intensities measured with a substrate with straight pores and with tapered pores.

The substrate 18 using silicon has been used to manufacture flow-through chips on which different probes have been immobilized in discrete regions or spots. The same flow-through chips have been manufactured with a highly microporous silicon substrate with pore walls normal to the surface. When these flow-through chips were hybridized with the same target molecules and processed with identical protocols to detect chemiluminescent labels attached to target molecules bound by the probes, the signal intensities were approximately 40% greater with the substrate described in this invention (FIG. 18). This experimental result confirms the theoretical evaluation of efficiency enhancement due to pore tapering. The enhanced optical detection sensitivity improves the sensitivity of assays performed on the chips and/or improves the throughput of the assay system.

The suggested approach is not very sensitive to a particular selection of the tapering angle as long as the inner plane of a pore wall does not restrict light collection. For the parameters listed above the tapering angle can be selected in the range between 0.3 degrees (tapering of a pore wall along full pore depth) to approximately 14 degrees. Tapering with the angles outside of this range will still increase amount of collected light, but the improvement will be less pronounced. It is noted that selection of a particular tapering angle and depth of tapering can be additionally influenced by the process of substrate manufacturing, the selected pore size and membrane thickness.

Figure 19B:
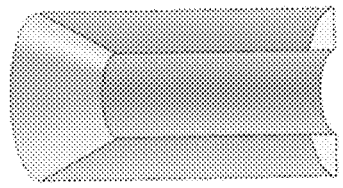
FIG. 19B shows a section of a single pore of the embodiment of FIG. 19A.
Figure 19A:
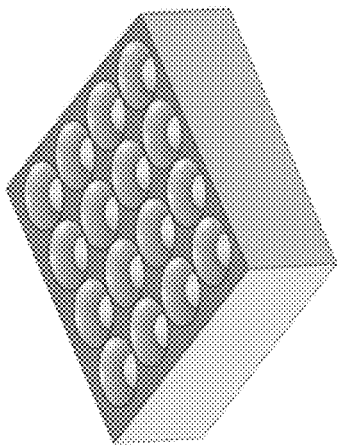
FIG. 19A shows another embodiment of the flow-through chip substrate with cylindrical pores with conical tapering.
Figure 20B:
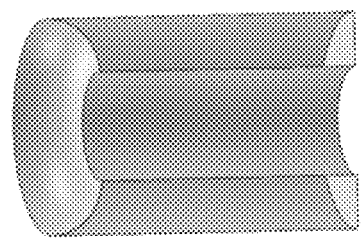
FIG. 20B shows a section of a single pore of the embodiment of FIG. 20A.
Figure 20A:
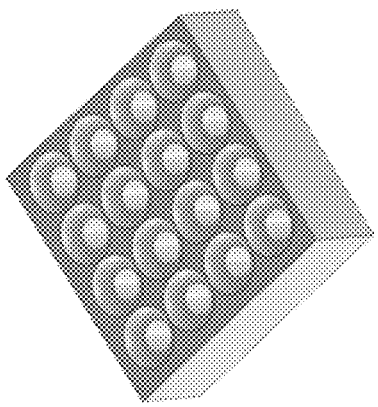
FIG. 20A shows another embodiment of the flow-through chip substrate with cylindrical pores with spherical tapering.
Figure 21A:
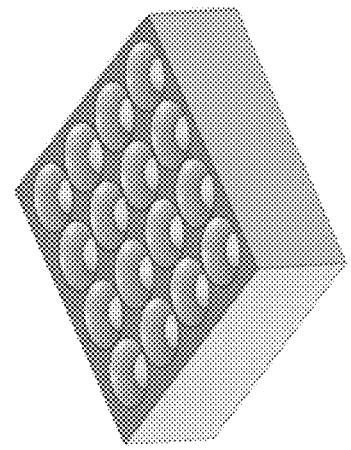
FIG. 21A shows another embodiment of the flow-through chip substrate with cylindrical pores with parabolic tapering.
Figure 21B:
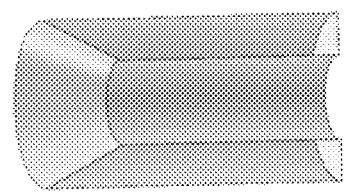
FIG. 21B shows a section of a single pore of the embodiment of FIG. 21A.

The geometry of pores does not need to be square. If the manufacturing process requires they may have a different cross section, for example, circular. In this case the pore is cylindrical (see FIGS. 19A, 19B to 21A, 21B inclusive). In this case the simplest form of tapering is conical as shown in FIGS. 19A and 19B. The light collection efficiency can be additionally increased by changing shape of tapering from conical to spherical (see FIGS. 20A and 20B) or parabolic (FIGS. 21A and 21B).

Figure 13A:
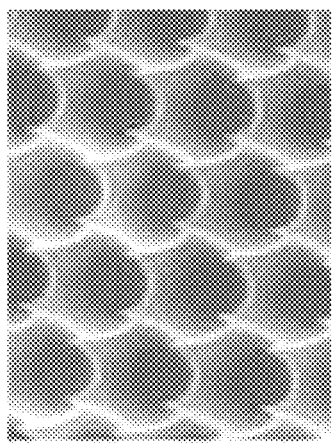
FIGS. 13A to 13C show micro photographs of the substrates with pores of a different cross section with FIG. 13A being circular, FIG. 13B being square, and FIG. 13C being polygonal.
Figure 13B:
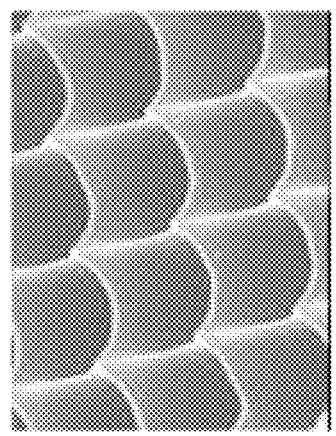
Figure 13C:
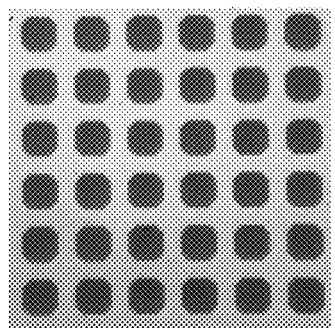
Figure 14C:
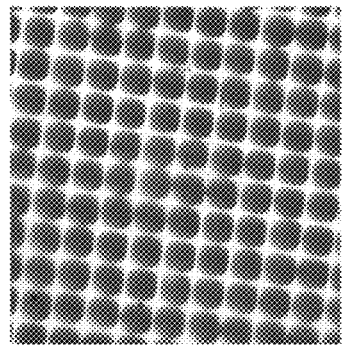
FIGS. 14A to 14C show the tapered pores with different angles of tapering and as a result with different depths of tapered portion of a pore, with the optical micrographs showing the cross sections of tapered pores with different angles of tapering 14A, 14B and the top view, 14C of the substrate cross section of which is shown in FIG. 14A.
Figure 14B:
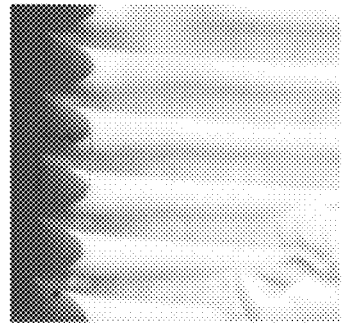
Figure 14A:
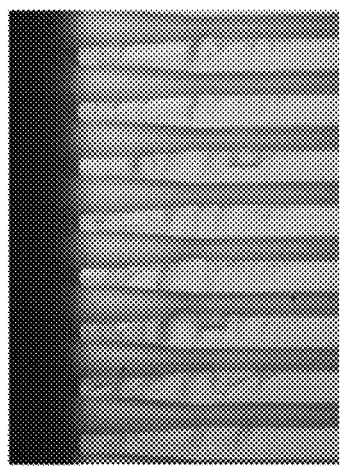

Pores of different cross section (circular, square, polygonal) were derived to practice: the micro photographs of such silicon substrates are shown in FIGS. 13A to 13C. The light collection efficiency can be additionally improved for a substrate with cylindrical pores by a denser arrangement of pores as shown in FIG. 22B compared to the collection efficiency of the packed structure of FIG. 22A.

Figure 23:
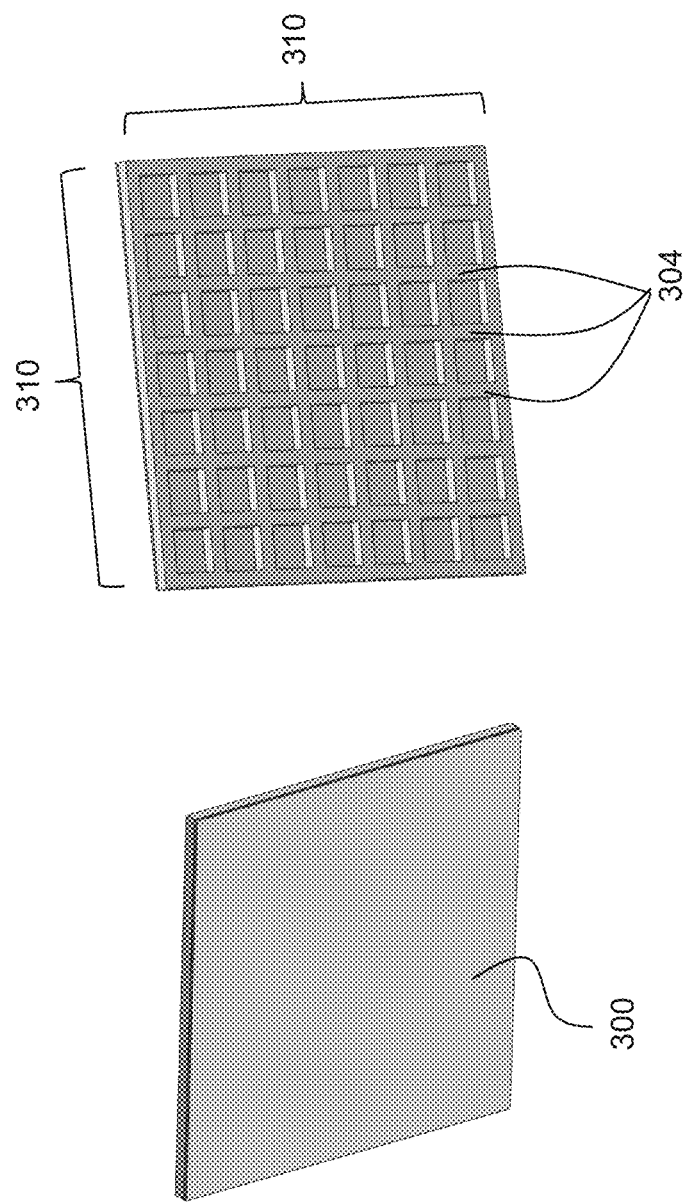
FIG. 23 shows an embodiment of the flow-through chip substrate with the high-efficiency microporous substrate on the left hand side reinforced by a frame for structural stability, shown on the right hand side of the figure.
Figure 24:
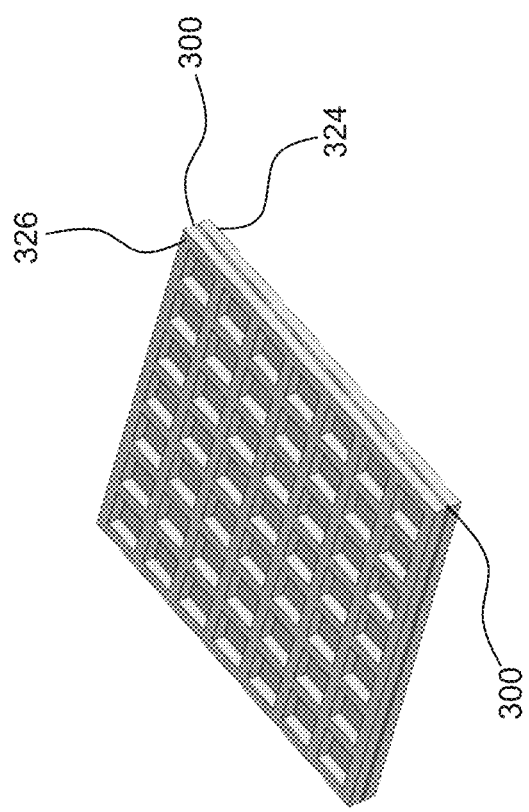
FIG. 24 shows another embodiment of a flow-through chip substrate for improved optical detection sensitivity with a high-efficiency microporous substrate reinforced by two frames placed on the opposite sides of the substrate for structural stability.

The structural stability of the substrate material depends on the type of material (e.g. silicon or plastic) and its thickness. If the substrate is thin or/and the material is flexible or soft, a reinforcement frame can be used to strengthen the substrate (see FIGS. 23 and 24). Referring to FIG. 23, a substrate 300 can be attached to a single frame 310 made of ribs 304 with the single frame being integrally formed with the substrate 300 or, preferably sandwiched between two separate frames 324 and 326 (see FIG. 24), which are separate from the substrate 300, to allow bidirectional application of pressure required to drive fluids through the porous substrate as described above without damaging of the substrate.

in conclusion, the present disclosure provides a disposable sample handling cartridge for performing multiplex biological assays in which the cartridge is designed and configured to provide complex fluid processing without the need for active pumping and valving. The cartridge is readily produced using standard molding techniques, no nanostructrures are required and no precise tolerances are required. The movement of sample and reagent fluid is solely determined by application of differential pressures, which are correlated primarily with the properties of the sample substrate 18, namely pore size and distribution in the substrate 18, as well as the inner diameter of the capillary channels (e,g. 48). The cartridge disclosed herein advantageously contains no moving parts and is made of a small number of parts compared to current systems, which typically contain active pumps, active valves and the like.

The cartridge disclosed herein may be used for, but is not limited to use in sandwich, or competitive immunoassay for protein antigen analysis; serology for antibody binding to immobilized antigens for allergy, autoimmune, infectious disease; nucleic acids measurement of DNA, RNA, mRNA, microRNA (miRNA) etc. to identify specific sequences whose presence or expression is correlated to presence or progress of disease, sequences that can be used to identify species of bacteria, fungi, viruses in a sample, sequences that indicated the presence of specific resistance genes in pathogens, measurement of copy number variations (CNV's) or specific gene variants or deletions that correlate to risk of disease, gene signatures used to type samples for forensic or identification purposes. In addition, it may be used for small molecule measurements including drugs and environmental contaminants. It may also be used in multiple sample matrices including human and animal fluids and tissues, food and agricultural samples, environmental samples, cells and lysates of cells, and bioprocessing fluids.

Non-limiting exemplary uses of the disposable cartridge disclosed herein will now be given using a nucleic acid assay and a protein assay.

EXAMPLES

Figure 25A:
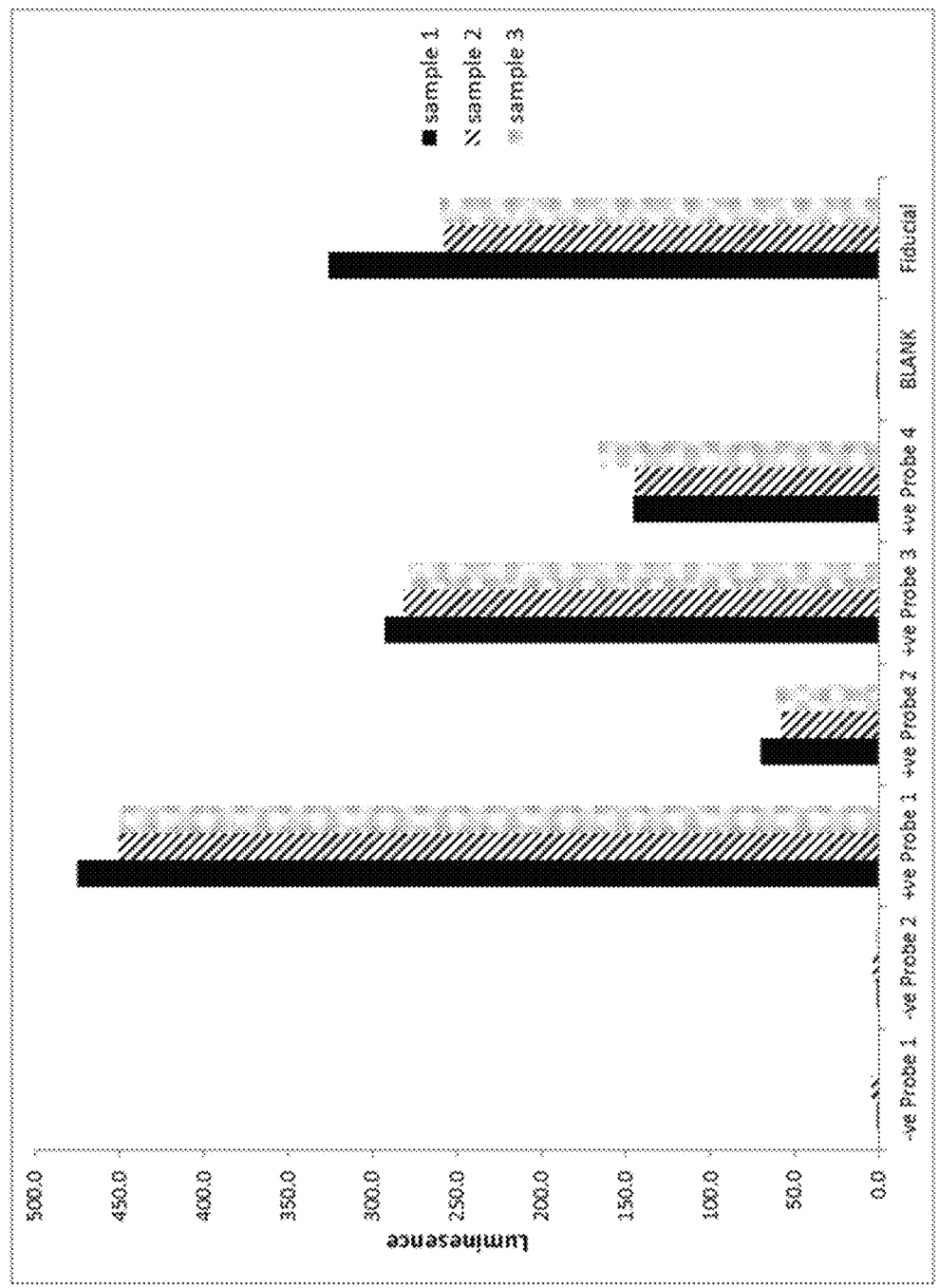
FIG. 25A shows results of a nucleic acid bioassay conducted using the assembled cartridge shown in FIG. 7.
Figure 25B:
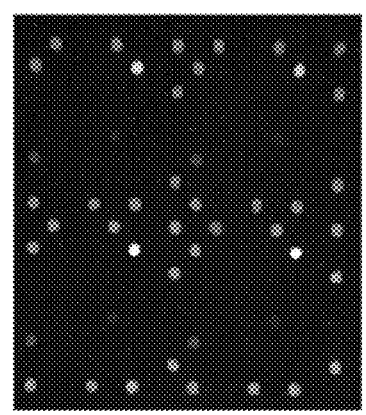
FIG. 25B shows the chemiluminescent image of the microporous substrate contained within the assembled cartridge shown in FIG. 7 at the conclusion of the nucleic acid bioassay
Figure 27B:
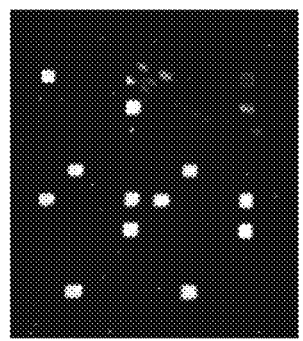
FIG. 27B shows the chemiluminescent image of a microporous substrate used to detect residual protein analytes in a solution processed by a separate microporous substrate configured for sample preparation.
Figure 27C:
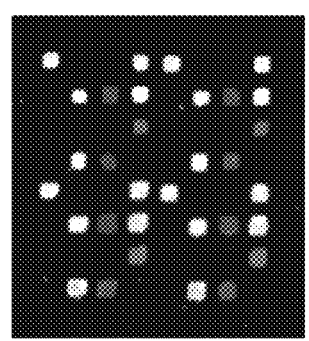
FIG. 27C shows the chemiluminescent image of a microporous substrate used to detect residual protein analytes in a solution prior to processing by a separate microporous substrate configured for sample preparation.
Figure 27A:
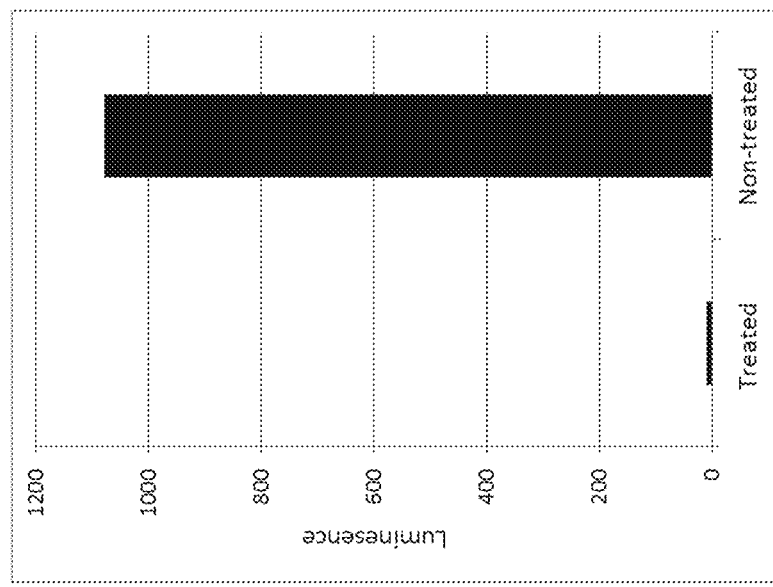
FIG. 27A shows results of a sample preparation using a microporous substrate forming part of the present cartridge.

FIG. 25A shows results of a nucleic acid bioassay wherein a sample containing biotin labelled PCR products representing copies of specific gene sequences from bacterial samples were processed using the cartridge shown in FIG. 7. Prior to assembly of the cartridge, the microporous substrate 18 was functionalized in discrete regions to form analysis spots, each of approximately 200 um in diameter, with oligonucleotide probes containing sequences complementary to sequences known to occur in the amplified bacterial gene (+ve Probes 1, 2, 3, 4), sequences not known to occur in the amplified bacterial gene (−ve Probes 1, 2) or a sequence complementary to an artificial oligonucleotide added to the sample (Fiducial). In addition, one blank spot where no oligonucleotide probe was immobilized was used as a control to measure background signal. 5 individual reagent wells 10 and a bulk chamber 87 were used.

The reagent chambers were individually loaded with blocking buffer, hybridization buffer, sample, streptavidin-HRP and chemiluminescent substrate respectively. The bulk reservoir 87 was loaded with wash buffer. Reagents were transferred to the upper processing chamber in individual steps as illustrated in FIG. 3. Each liquid was then transferred to the lower processing chamber as illustrated in FIG. 4 and then returned to the upper processing chamber as illustrated in FIG. 5.

After repeating this cycle back and forth through the microporous substrate 18 as many times as required for each step the reagent was removed to waste chamber as illustrated in FIG. 6. Between each step an aliquot of wash buffer from bulk chamber 87 was similarly processed. The sequential steps accomplished blocking of the porous microporous substrate to prevent non-specific binding, hybridization of PCR products in the sample to the probes containing complementary sequences immobilized in discrete regions on porous substrate 18, binding of streptavidin-HRP to the biotin label on captured PCR products, and introduction of a chemiluminescent substrate that could be processed by the captured HRP enzyme to produce a chemiluminescent emission in that specific region.

During the final step, an image of the microporous substrate 18 was captured with a CCD camera 120 located below the optical window 40. This image FIG. 25B was analyzed for intensity of light measured across the microporous substrate 18 and correlated to the specific regions known to contain the immobilized probes. FIG. 25A shows the luminescent intensity for three repeats of the bioassay for the same sample. It will be noted that significant signals are observed on analysis spots formed by immobilizing probes containing complementary sequences to gene sequences expected in the sample (+ve Probes 1, 2, 3, 4), minimal signal is observed on analysis spots formed by immobilizing probes containing complementary sequences to gene sequences not expected in the sample (−ve Probes 1, 2). As expected, no signal was observed on the blank analysis spot, and substantial signal was observed on the analysis spot containing a complementary sequence to the artificial oligonucleotide added to the sample prior to analysis.

FIG. 26 shows results of protein bioassays on human serum or control buffer to determine the presence of antibodies against the measles virus carried out using the cartridge pictured in FIG. 7. Prior to assembly of the cartridge, the microporous substrate 18 was functionalized in discrete regions to form analysis spots, each of approximately 200 um in diameter, with a deactivated measles virus preparation. Four reagent chambers were individually loaded with blocking buffer, sample, HRP labelled anti human immunoglobulin G and chemiluminescent substrate, respectively. The bulk reservoir 87 was loaded with wash buffer.

Reagents were transferred to the upper processing chamber in individual steps as illustrated in FIG. 3. Each liquid was then transferred to the lower processing chamber as illustrated in FIG. 4 and then returned to the upper processing chamber as illustrated in FIG. 5. After repeating this cycle back and forth through the microporous substrate 18 as many times as required for each step the reagent was removed to waste chamber as illustrated in FIG. 6. Between each step an aliquot of wash buffer from bulk chamber 87 was similarly processed. The sequential steps accomplished blocking of the microporous substrate to prevent non-specific binding, binding from the sample of any immunoglobulins containing regions that are specific to components of the measles virus immobilized in discrete regions on microporous substrate 18, binding of anti-human immunoglobulin G antibody coupled to a HRP enzyme to any retained anti-measles immunoglobulins, and introduction of a chemiluminescent substrate that could be processed by the bound HRP enzyme to produce a chemiluminescent emission in that specific region.

During the final step, an image of the porous microporous substrate 18 was captured with a CCD camera 120 located below the optical window 40. This image was analyzed for intensity of light measured across the microporous substrate 18 and correlated to the specific regions known to contain the immobilized virus. The chart in FIG. 26 shows the luminescence intensity recorded for three types of samples. It will be noted that significant signal corresponding to the presence of measles specific antibodies is observed from the serum sample drawn from a patient known to have immunity to the measles virus (positive serum). Significantly lower signal is observed from serum drawn from a patient known to have reduced immunity to the measles virus (negative serum). Minimal signal is observed from a control buffer sample that does not contain any measles specific antibodies.

FIG. 27A illustrates the results of a process that utilizes two different microporous substrates each with upper and processing chambers, one of which is a solid support for capture of protein analytes, and the other of which is a microporous substrate on which the protein analytes are detected on bound protein specific receptors. In this example, identical samples containing biotinylated mouse IgG analyte were cycled through a microporous substrate 18 that was functionalized with a rabbit anti-mouse antibody know to have a high binding affinity for mouse IgG (Treated sample) or cycled through a microporous substrate 18 that had not been functionalized, (Non-treated sample).

The resulting fluid was then processed through a microporous substrate that had been functionalized in discrete regions to form analysis spots, each of approximately 200 um in diameter with either a rabbit anti-mouse antibody known to have a high binding affinity for mouse IgG or a biotinylated bovine serum albumin to serve as a reference spot. Washing, binding of streptavidin-HRP to any captured biotin-mouse IgG and immobilized biotin-BSA, and introduction of a chemiluminescent substrate that could be processed by the bound HRP enzyme to produce a chemiluminescent emission in that specific region were sequentially carried out. During the final step, an image of the microporous substrate 18 was captured with a CCD camera 120 located below the optical window 40. The intensity of each spot functionalized with rabbit anti-mouse IgG correlates with the amount of biotinylated mouse IgG analyte present in the solution.

FIG. 27A shows that the sample that had been processed by the first functionalized microporous substrate 18 (Treated) was almost completely depleted of mouse IgG analyte when processed on the second microporous substrate 18 used for detection. It can also be observed that the sample that had been processed by the first non-functionalized microporous substrate 18 (Non-treated) exhibited high levels of mouse IgG analyte when processed on the second microporous substrate 18 used for detection.

FIG. 27B represents the signal captured by the CCD camera 120 from the second microporous substrate 18 for the treated sample. Significant signal is observed only on the reference biotinylated BSA analysis spots. FIG. 27C represents the signal captured by the CCD camera 120 from the second microporous substrate 18 for the non-treated sample. Significant signal from the analysis spots for both the reference biotinylated BSA and the biotinylated mouse IgG can be observed. This illustrates the high efficiency of using a first microporous substrate 18 functionalized with analyte specific reagents to deplete those analytes prior to detection and quantitation on a second microporous substrate 18. As an example, this may have utility in removing or depleting substances that may interfere with analysis on the second microporous substrate 18.

Therefore what is claimed is:

1. A system for detection of analytes present in liquid samples, comprising:

a light detector; and a generally planar microporous substrate material having opposed surfaces and tapered micropores extending completely through a thickness of said microporous substrate, and wherein ends of the tapered micropores have larger micropore openings on one surface of the microporous substrate compared to smaller pore openings on the opposed surface;

analyte-specific receptors to the analytes bound inside the micropores to walls of the tapered micropores having the wider pore openings, said analyte-specific receptors emit light when analytes in the liquid sample bind to the analyte specific sensors; and said microporous substrate being spaced from said light detector with said light detector facing the surface of said microporous substrate having the larger micropore openings to provide an increase in collection efficiency of light emitted from analyte-specific receptors in said micropores detected by said light detector compared to a light collection efficiency of light emitted from the analyte-specific receptors when the micropores are straight and not tapered.

2. The microporous substrate according to claim 1 in which the tapered micropores are progressively wider near said one surface of the substrate.

3. The microporous substrate according to claim 1 in which the tapered micropores have a rectangular cross section.

4. The microporous substrate according to claim 1 in which the tapered micropores have a square cross section.

5. The microporous substrate according to claim 1 in which the tapered micropores have a circular cross section.

6. The microporous substrate according to claim 5 in which the tapered micropores with the circular cross section are conical.

7. The microporous substrate according to claim 1 in which the tapered micropores dimension on the side opposite the side of the larger micropore openings are substantially smaller thereby providing structural stability to the microporous substrate.

8. The microporous substrate according to claim 1 in which the tapered micropores are of uniform dimensions and morphology.

9. The microporous substrate according to claim 1 further comprising reinforcement ribs to provide structural stability.

10. The microporous substrate according to claim 9 in which the reinforcement ribs are an integral part of the substrate.

11. The microporous substrate according to claim 9 in which the reinforcement ribs are separate from the microporous substrate and made in a form of a rigid first supporting mesh, wherein said microporous substrate is attached to said rigid supporting mesh.

12. The microporous substrate according to claim 11 wherein said microporous substrate is attached to said rigid supporting mesh placed on the surface of the said microporous substrate at which the narrower ends of the tapered micropores are located.

13. The microporous substrate as in claim 12 including a second supporting mesh located on the opposed surface to which said first supporting mesh is attached.

14. The microporous substrate according to claim 1 having a thickness of between about 0.15 mm to about 0.75 mm.

15. The microporous substrate according to claim 1 in which the tapered surface of the micropores are coated with a reflective coating.

16. The microporous substrate according to claim 1 made of silicon.

17. The microporous substrate according to claim 1 manufactured by electrochemical etching of silicon.

18. The microporous substrate according to claim 1 manufactured by embossing or molding of a plastic material.

19. The microporous substrate according to claim 1 wherein the porous substrate material is opaque such that light from one micropore cannot be transmitted to neighboring micropores with the microporous substrate.

20. The microporous substrate according to claim 1 wherein said tapered micropores have a size in a range from about 1 micron to about 15 microns, and wherein a tapering angle of said tapered micropores is in a range from about 0.3 degrees to about 14 degrees, and wherein a wall thickness of the microporous substrate between the tapered micropores is in a range from about 1 to about 5 microns.

* * * * *